United States Patent [19]

Hayashi et al.

[11] Patent Number: 4,698,094
[45] Date of Patent: Oct. 6, 1987

[54] 2-NITRO-5-(2'CHLORO-4'TRIFLUOROME-THYLPHENOXY)-PHENYLACETIC ESTERS, HERBICIDAL COMPOSITION, AND METHOD FOR DESTRUCTION OF UNDESIRABLE WEEDS

[75] Inventors: Yoshiharu Hayashi; Hiroyuki Kouji, both of Yokohama, Japan

[73] Assignee: Asahi Kasei Kogyo Kabushiki Kaisha, Osaka, Japan

[21] Appl. No.: 725,537

[22] Filed: Apr. 22, 1985

[30] Foreign Application Priority Data

May 18, 1984 [JP] Japan ................................. 59-100061
May 18, 1984 [JP] Japan ................................. 59-100062
May 18, 1984 [JP] Japan ................................. 59-100063
May 21, 1984 [JP] Japan ................................. 59-102372

[51] Int. Cl.⁴ ..................... A01N 37/40; C07C 79/46
[52] U.S. Cl. ........................................ 71/108; 560/21
[58] Field of Search ............... 560/23, 21; 558/398; 549/551; 71/98, 105, 111, 108

[56] References Cited

U.S. PATENT DOCUMENTS 3,888,932  6/1975  Bayer et al. ................. 260/612 R
3,928,416  12/1975 Bayer et al. ................. 260/471 R
4,076,741  2/1978  Bayer et al. ................. 260/465 F
4,419,123  12/1983 Swithenbank ................. 71/98

Primary Examiner—Dolph H. Torrence
Attorney, Agent, or Firm—Birch, Stewart, Kolasch & Birch

[57] ABSTRACT

Phenylacetic esters, thioesters and amides of the formula

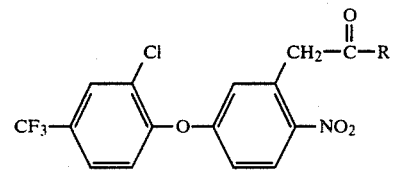

wherein R is as defined in the disclosure, process for preparation thereof, herbicidal composition and method for destruction of undesirable weeds. The herbicides comprising the above compounds are capable of selectively controlling undesirable weeds among desirable crop plants.

17 Claims, No Drawings

2-NITRO-5-(2'CHLORO-4'TRIFLUOROMETHYL-PHENOXY)-PHENYLACETIC ESTERS, HERBICIDAL COMPOSITION, AND METHOD FOR DESTRUCTION OF UNDESIRABLE WEEDS

FIELD OF THE INVENTION

This invention relates to a novel compound which exhibits a selective herbicidal activity, a novel process for preparation thereof, a novel herbicidal composition comprising the novel compound which is useful as an effective herbicide for various crops and a novel method for destruction of undesirable weeds using the novel composition. More particularly, the present invention is concerned with 2-nitro-5-(2'-chloro-4'-trifluoromethylphenoxy)phenylacetic ester, thioester and amide, a process for preparation of such compounds, a herbicidal composition comprising such compounds and a method for destruction of undesirable weeds using the composition.

STATE OF THE PRIOR ART

To now, a herbicide comprising as an active ingredient 4-nitro-2'-chloro-4'-trifluoromethyldiphenyl ether having, bonded thereto at its 3-position, a substituent such as hydroxyl group, alkoxy group, alkyl group, halogen atom, amino group, cyano group, carboxyl group, carboalkoxy group, carboxyalkyl group, alkanoyloxy group and carbamoyloxy group or other diphenyl ether derivatives is well known as the generally called diphenyl ether type herbicide (see, for example, Japanese Patent Application Publication No. 58-25641/1983 corresponding to U.S. Pat. Nos. 3,789,276, 3,888,932, 3,928,416 and 4,076,741).

However, any of the known diphenyl ether herbicides generally tends to be either excellent in herbicidal activity but poor in selectivity or excellent in selectivity but poor in herbicidal activity. Hence, any of them is not suitable for effective and prompt control of only predetermined species of weeds.

The ideal herbicide should be one which satisfies the following requirements in addition to the above-stated excellent herbicidal activity and high selectivity. The toxicity of the herbicide to warm-blooded animals must be low. The herbicide is expected to be usable through the whole period of growth of crop plants. Moreover, after usage, the herbicide is expected to decompose as promptly as possible so that it does not contaminate the soil. However, such an ideal diphenyl ether herbicide which satisfies the above requirements is not yet known.

OBJECT OF THE PRESENT INVENTION

Under the above-stated current situation, the inventors have made intensive studies to develop a novel diphenyl ether herbicide which is free from the drawbacks of the conventional diphenyl ether herbicides, which has selective and highly effective herbicidal activity that means complete safety to crop plants and prompt elimination of any unnecessary plants present therewith, which can be used continuously through the whole period of growth of crop plants. As a result, it has been found that novel compounds of 2-nitro-5-(2'-chloro-4'-trifluoromethylphenoxy)phenylacetic ester, thioester and amide satisfy the above-mentioned requirements for an improved herbicide, and that the compound, even at a low dosage, is very useful for a broad spectrum of crop plants, such as cotton, soybean, corn, wheat and rice plants. Based on this novel finding, the present invention has been completed.

Accordingly, it is an object of the present invention to provide novel compounds of 2-nitro-5-(2'-chloro-4'-trifluoromethylphenoxy)phenylacetic esters, thioesters and amides having a highly selective herbicidal activity.

It is another object of the present invention to provide a novel process for preparation of such compounds.

It is a further object of the present invention to provide a novel herbicidal composition having a high selectivity, which is capable of obviating the drawbacks accompanying the conventional diphenyl ether type herbicides and can be applied to a broad spectrum of crop plants regardless of the growing period.

It is a still further object of the present invention to provide a novel method for destruction of undesirable weeds using the novel composition. The foregoing and other objects, features and advantages of the present invention will be apparent to those skilled in the art from the following detailed description and appended claims.

In one aspect of this invention, there is provided a compound represented by the formula

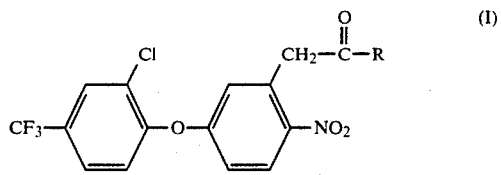

wherein
R represents $-OR^1$, $-SR^2$ or

in which $R^1$ represents an aliphatic ethylenically or acetylenically unsaturated hydrocarbon residue, an aromatic hydrocarbon residue, an aroaliphatic hydrocarbon residue, a straight or branched alkyl or alkenyl group, said alkyl or alkenyl group being substituted with at least one member selected from the group consisting of a halogen atom, a cyano group, a hydroxyl group, a mercapto group, a hydrocarbyloxy group, a hydrocarbylthio group, an epoxy group, an acyl group, an acyloxy group, an acylthio group, a substituted or unsubstituted amino group and a hetero cyclic group, or a straight or branched alkyl group substituted with at least one member selected from the group consisting of a carboxyl group and a group functionally derived therefrom;

$R^2$ represents a hydrocarbon residue, a straight or branched alkyl or alkenyl group, said alkyl or alkenyl group being substituted with at least one member selected from the group consisting of a halogen atom, a cyano group, a hydroxyl group, a mercapto group, a hydrocarbyloxy group, a hydrocarbylthio group, an epoxy group, an acyl group, an acyloxy group, an acylthio group, a substituted or unsubstituted amino group and a hetero cyclic group, or a straight or branched alkyl group substituted with at least one member selected from the group consisting of a carboxyl group and a group functionally derived therefrom; and R$^3$ and R$^4$ each independently represent a hydrogen atom, a hydrocarbyloxy group or a hydrocarbon residue, said hydrocarbon residue being unsubstituted or substituted with at least one member selected from the group consisting of a halogen atom, a hydroxyl group and a cyano group and containing or not containing at least one combination of two neighboring carbon atoms having an oxygen atom or a sulfur atom inserted therebetween.

It is surprising that the compounds described above provide a preemergence or postemergence herbicide which is very effective for control of unwanted weeds in culture of a broad spectrum of crop plants even at a far lower dosage than that of the conventional compounds having similar structures.

The characteristic feature of the compound of the present invention resides in that it has a group represented by R as shown in the above-indicated formula. Illustratively stated, the conventional compounds are such compounds in which the group in a position corresponding to that of R above is a lower alkyl group such as methyl group which does not have any substitutents. By contrast, the compound of the present invention is a compound represented by the above-indicated formula in which R represents —OR$^1$, —SR$^2$ or

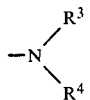

wherein p1 R$^1$ represents an aliphatic ethylenically or acetylenically unsaturated hydrocarbon residue, an alicyclic hydrocarbon residue, an aromatic hydrocarbon resudue, an aroaliphatic hydrocarbon residue, a straight or branched alkyl or alkenyl group, said alkyl or alkenyl group being substituted with at least one member selected from the group consisting of a halogen atom, a cyano group, a hydroxyl group, a mercapto group, a hydrocarbyloxy group, a hydrocarbylthio group, an epoxy group, an acyl group, an acyloxy group, an acylthio group, a substituted or unsubstituted amino group and a hetero cyclic group, or a straight or branched alkyl group substituted with at least one member selected from the group consisting of a carboxyl group and a group functionally derived therefrom;

R$^2$ represents a hydrocarbon residue, a straight or branched alkyl or alkenyl group, said alkyl or alkenyl group being substituted with at least one member selected from the group consisting of a halogen atom, a cyano group, a hydroxyl group, a mercapto group, a hydrocarbyloxy group, a hydrocarbylthio group, an epoxy group, an acyl group, an acyloxy group, an acylthio group, a substituted or unsubstituted amino group and a hetero cyclic group, or a straight or branched alkyl group substituted with at least one member selected from the group consisting of a carboxyl group and a group functionally derived therefrom; and R$^3$ and R$^4$ each independently represent a hydrogen atom, a hydrocarbyloxy group or a hydrocarbon residue, said hydrocarbon residue being unsubstituted or substituted with at least one member selected from the group consisting of a halogen atom, a hydroxyl group and a cyano group and containing or not containing at least one combination of two neighboring carbon atoms having an oxygen atom or a sulfur atom inserted therebetween.

Suitable examples of the above-mentioned R$^1$ and R$^2$ may be an allyl group, 2-butynyl group, cyclopentyl group, cyclohexyl group, phenyl group and benzyl group. In the case of an aromatic ring-bearing group among these groups, it may be a substituted one.

The above-mentioned ethylenically or acetylenically unsaturated hydrocarbon residue may be a straight chain or branched one. As the suitable halogen atom, there may be mentioned, for example, a fluorine atom, chlorine atom, bromine atom and iodine atom. The hydrocarbyloxy group is a group having such a structure that the hydrogen atom of the hydroxyl group is substituted by a hydrocarbon residue such as alkyl group, alkenyl group, alkynyl group, aryl group and aralkyl group. If the hydrocarbon group has an aromatic ring, such an aromatic ring may further have a substituent.

As the suitable hydrocarbyloxy group, there may be mentioned, for example, a methoxy group, ethoxy group, allyloxy group, propionyloxy group, benzyloxy group, p-methylbenzyloxy group and the like. The hydrocarbylthio group is a group having such a structure that the oxygen atom of the hydrocarbyloxy group is replaced by a sulfur atom. As the suitable hydrocarbylthio group, there may be mentioned, for example, a methylthio group, ethylthio group, allythio group, benzylthio group and the like. The above-mentioned acyl group, acyloxy group and acylthio group may be either aliphatic or aromatic, and may have a substituent. Specific examples of these groups are an acetyl group, propionyl group, benzoyl group, acetyloxy group, butyroyloxy group, acetylthio group and the like. The substituted amino group may be either a mono-substituted group or a di-substituted group. As the suitable substituted amino group, there may be mentioned, for example, a monomethylamino group, dimethylamino group, monoethylamino group, diethylamino group, methylethylamino group, methylmethoxyamino group and the like.

The above-mentioned heterocyclic group may be in a completely unsaturated form or in a partially or entirely saturated form. As the suitable heterocyclic group, there may be mentioned, for example, groups derived from a thiophene, furan, pyrrole, pyridine, quinoline, piperazine, imidazole and hydrides thereof.

Further, suitable examples of the above-mentioned R$^1$ and R$^2$ may be a straight or branched alkyl group having as a substituent a carboxyl group or a group functionally derived therefrom.

The term "a group functionally derived" is intended to mean a group derived from a carboxyl group which was obtained by converting only the carboxyl group in a carboxylic compound and which can be generally classified in the same category as that of a carboxyl group. As examples of such group, there may be mentioned a carboxylate group, carboxylic acid ester group, acid halide group, acid amide group and the like. These groups may be readily derived from a carboxyl group according to customary procedures, and may be converted to the original carboxyl group by hydrolysis.

Examples of $R^1$ and $R^2$ in the compound of the present invention may be straight or branched alkyl groups having as a substituent a group represented by the formula

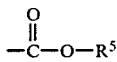

wherein
$R^5$ represents a hydrogen atom, a substituted or unsubstituted alkyl group, a substituted or unsubstituted alkenyl group, an alkynyl group, an alkali metal, an alkaline earth metal in proportion corresponding to mono-valency of the alkaline earth metal, ammonium group or an alkyl-substituted ammonium group

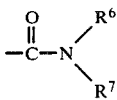

wherein
$R^6$ and $R^7$ each independently represent a hydrogen atom, an alkyl group or an alkoxy group.

The examples of substitutents which may be contained in a substituted or unsubstituted alkyl group or alkenyl group represented by $R^5$ according to need are a halogen atom, cyano group, lower alkoxy group, alkenyloxy group, alkylthio group, alkenylthio group, alkynylthio group, hydroxyl group, aliphatic acyl group, carboxylate group, alkoxycarbonyl group, alkoxyalkoxycarbonyl group, aminocarbonyl group and the like.

Moreover, suitable examples of $R^2$ may be a straight or branched alkyl group such as methyl group, ethyl group, propyl group, butyl group and isopropyl group.

Suitable examples of the above-mentioned $R^3$ and $R^4$ may be a hydrogen atom, a hydrocarbon residue such as aliphatic hydrocarbon residue, aromatic hydrocarbon residue, araliphatic hydrocarbon residue or alicyclic hydrocarbon residue or a hydrocarbyloxy group wherein the above hydrocarbon residue is bonded to an oxygen atom. In this connection, the above-mentioned aliphatic hydrocarbon residue may be a saturated or an unsaturated one, or a straight-chain or a branched-chain one. It may have an oxygen atom or a sulfur atom inserted between two neighboring carbon atoms at least at one portion thereof so as to form an ether bond or a thioether bond. The above-mentioned hydrocarbon residue may be substituted with at least one member selected from the group consisting of a halogen atom, a hydroxyl group and a cyano group.

As examples of the above-mentioned $R^3$ and $R^4$, there may be mentioned a hydrogen atom, methyl group, ethyl group, n-propyl group, isopropyl group, n-butyl group, isobutyl group, n-pentyl group, n-hexyl group, n-heptyl group, 2-propenyl group, 2-propynyl group, 3-butenyl group, cycloheptyl group, cyclohexyl group, phenyl group, tolyl group, benzyl group, 2-methoxyethyl group, 2-ethoxyethyl group, 3-methoxypropyl group, 2-butoxyethyl group, 2-methylmercaptoethyl group, 2-butylmercaptoethyl group, 2-benzylmercaptoethyl group, 2-hydroxypropyl group, 2-hydroxybutyl group, 3-hydroxypropyl group, 2-chloroethyl group, 2-bromoethyl group, p-chlorophenyl group, cyanomethyl group, 2-cyanomethyl group, methoxy group, ethoxy group, allyloxy group, benzyloxy group and the like.

As specific examples of the compound of the present invention represented by the above-mentioned formula (I), there may be mentioned:
S-methyl 2-nitro-5-(2'-chloro-4'-trifluoromethylphenoxy)phenylthioacetate,
S-ethyl 2-nitro-5-(2'-chloro-4'-trifluoromethylphenoxy)phenylthioacetate,
S-1-methylethyl 2-nitro-5-(2'-chloro-4'-trifluoromethylphenoxy)phenylthioacetate,
S-2-propenyl 2-nitro-5-(2'-chloro-4'-trifluoromethylphenoxy)phenylthioacetate,
S-2-propynyl 2-nitro-5-(2'-chloro-4'-trifluoromethylphenoxy)phenylthioacetate,
S-cyclopropyl 2-nitro-5-(2'-chloro-4'-trifluoromethylphenoxy)phenylthioacetate,
S-cyclohexyl 2-nitro-5-(2'-chloro-4'-trifluoropropylphenoxy)phenylthioacetate,
2-propenyl 2-nitro-5-(2'-chloro-4'-trifluoromethylphenoxy)phenylacetate,
2-propynyl 2-nitro-5-(2'-chloro-4'-trifluoromethylphenoxy)phenylacetate,
cyclopropyl 2-nitro-5-(2'-chloro-4'-trifluoromethylphenoxy)phenylacetate,
cyclohexyl 2-nitro-5-(2'-chloro-4'-trifluoromethylphenoxy)phenylacetate,
S-phenyl 2-nitro-5-(2'-chloro-4'-trifluoromethylphenoxy)phenylthioacetate,
S-4-chlorophenyl 2-nitro-5-(2'-chloro-4'-trifluoromethylphenoxy)phenylthioacetate,
S-4-methylphenyl 2-nitro-5-(2'-chloro-4'-trifluoromethylphenoxy)phenylthioacetate,
S-4-methoxyphenyl 2-nitro-5-(2'-chloro-4'-trifluoromethylphenoxy)phenylthioacetate,
S-benzyl 2-nitro-5-(2'-chloro-4'-trifluoromethylphenoxy)phenylthioacetate,
1-methyl-2-propenyl 2-nitro-5-(2'-chloro-4'-trifluoromethylphenoxy)phenylacetate,
4-methoxycarbonylphenyl 2-nitro-5-(2'-chloro-4'-trifluoromethylphenoxy)phenylacetate,
2-chloroethyl 2-nitro-5-(2'-chloro-4'-trifluoromethylphenoxy)phenylacetate,
cyanomethyl 2-nitro-5-(2'-chloro-4'-trifluoromethylphenoxy)phenylacetate,
2-hydroxyethyl 2-nitro-5-(2'-chloro-4'-trifluoromethylphenoxy)phenylacetate,
S-2-chloroethyl 2-nitro-5-(2'-chloro-4'-trifluoromethylphenoxy)phenylthioacetate,
S-1-methyl-2-hydroxyethyl 2-nitro-5-(2'-chloro-4'-trifluoromethylphenoxy)phenylthioacetate,
2-(4-methoxybenzyloxy)ethyl 2-nitro-5-(2'-chloro-4'-trifluoromethylphenoxy)phenylacetate,
2,3-epoxypropyl 2-nitro-5-(2'-chloro-4'-trifluoromethylphenoxy)phenylacetate,
methylcarbonylmethyl 2-nitro-5-(2'-chloro-4'-trifluoromethylphenoxy)phenylacetate,
S-2-methylcarbonylethyl 2-nitro-5-(2'-chloro-4'-trifluoromethylphenoxy)phenylthioacetate,
2-phenylcarbonylethyl 2-nitro-5-(2'-chloro-4'-trifluoromethylphenoxy)phenylacetate,
2-acetoxyethyl 2-nitro-5-(2'-chloro-4'-trifluoromethylphenoxy)phenylacetate,
2-benzoyloxyethyl 2-nitro-5-(2'-chloro-4'-trifluoromethylphenoxy)phenylacetate,
2-(N,N-dimethylamino)ethyl 2-nitro-5-(2'-chloro-4'-trifluoromethylphenoxy)phenylacetate, 2-(N-methyl-N-methoxyamino)ethyl 2-nitro-5-(2'-chloro-4'-trifluoromethylphenoxy)phenylacetate,
1-methoxyethyl 2-nitro-5-(2'-chloro-4'-trifluoromethylphenoxy)phenylacetate,
1-methyl-2-methylcarbonyloxyethyl 2-nitro-5-(2'-chloro-4'-trifluoromethylphenoxy)phenylacetate,
3-chloro-2-propenyl 2-nitro-5-(2'-chloro-4'-trifluoromethylphenoxy)phenylacetate,
N-methyl-4-piperidylmethyl 2-nitro-5-(2'-chloro-4'-trifluoromethylphenoxy)phenylacetate,
2-tetrahydropyranylmethyl 2-nitro-5-(2'-chloro-4'-trifluoromethylphenoxy)phenylacetate,
furfuryl 2-nitro-5-(2'-chloro-4'-trifluoromethylphenoxy)phenylacetate,
2-(2-thienyl)ethyl 2-nitro-5-(2'-chloro-4'-trifluoromethylphenoxy)phenylacetate,
3-(3-pyridyl)propyl 2-nitro-5-(2'-chloro-4'-trifluoromethylphenoxy)phenylacetate,
benzyl 2-nitro-5-(2'-chloro-4'-trifluoropropylphenoxy)phenylacetate,
4-methylbenzyl 2-nitro-5-(2',6'-dichloro-4'-trifluoromethylphenoxy)phenylacetate,
2-trifluoroacetoxyethyl 2-nitro-5-(2'-chloro-4'-trifluoromethylphenoxy)phenylacetate,
2-(2-chlorobenzoyloxy)ethyl 2-nitro-5-(2'-chloro-4'-trifluoromethylphenoxy)phenylacetate,
2-bromomethylcarbonylethyl 2-nitro-5-(2'-chloro-4'-trifluoromethylphenoxy)phenylacetate,
2-(3-methoxyphenylcarbonyl)ethyl 2-nitro-5-(2'-chloro-4'-trifluoromethylphenoxy)phenylacetate,
2-acetylthioethyl 2-nitro-5-(2'-chloro-4'-trifluoromethylphenoxy)phenylacetate,
2-benzoylthioethyl 2-nitro-5-(2'-chloro-4'-trifluoromethylphenoxy)phenylacetate,
2-methoxyethyl 2-nitro-5-(2'-chloro4'-trifluoromethylphenoxy)phenylacetate,
2-ethoxyethyl 2-nitro-5-(2'-chloro-4'-trifluoromethylphenoxy)phenylacetate,
2-(1-methylethoxy)ethyl 2-nitro-5-(2'-chloro-4'-trifluoromethylphenoxy)phenylacetate,
2-(2-propenyloxy)ethyl 2-nitro-5-(2'-chloro-4'-trifluoromethylphenoxy)phenylacetate,
2-(2-propynyloxy)ethyl 2-nitro-5-(2'-chloro-4'-trifluoromethylphenoxy)phenylacetate,
2--phenylmethoxyethyl 2-nitro-5-(2'-chloro-4'-trifluoromethylphenoxy)phenylacetate,
3-methoxypropyl 2-nitro-5-(2'-chloro-4'-trifluoromethylphenoxy)phenylacetate,
3-ethoxypropyl 2-nitro-5-(2'-chloro-4'-trifluoromethylphenoxy)phenylacetate,
3-(1-methylethoxy)propyl 2-nitro-5-(2'-chloro-4'-trifluoromethylphenoxy)phenylacetate,
3-(2-propenyloxy)propyl 2-nitro-5-(2'-chloro-4'-trifluoromethylphenoxy)phenylacetate,
1-methyl-2-methoxyethyl 2-nitro-5-(2'-chloro-4'-trifluoromethylphenoxy)phenylacetate,
2-ethoxy-1-methylethyl 2-nitro-5-(2'-chloro-4'-trifluoromethylphenoxy)phenylacetate,
1-methyl-2-(1-methylethoxy)ethyl 2-nitro-5-(2'-chloro-4'-trifluoromethylphenoxy)phenylacetate,
1-methyl-2-(2-propenyloxy)ethyl 2-nitro-5-(2'-chloro-4'-trifluoromethylphenoxy)phenylacetate,
methylthiomethyl 2-nitro-5-(2'-chloro-4'-trifluoromethylphenoxy)phenylacetate,
ethylthiomethyl 2-nitro-5-(2'-chloro-4'-trifluoromethylphenoxy)phenylacetate,
1-methylethylthiomethyl 2-nitro-5-(2'-chloro-4'-trifluoromethylphenoxy)phenylacetate,
2-propenylthiomethyl 2-nitro-5-(2'-chloro-4'-trifluoromethylphenoxy)phenylacetate,
2-propynylthiomethyl 2-nitro-5-(2'-chloro-4'-trifluoromethylphenoxy)phenylacetate,
2-methylthioethyl 2-nitro-5-(2'-chloro-4'-trifluoromethylphenoxy)phenylacetate,
2-ethylthioethyl 2-nitro-5-(2'-chloro-4'-trifluoromethylphenoxy)phenylacetate,
2-(2-propenylthio)ethyl 2-nitro-5-(2'-chloro-4'-trifluoromethylphenoxy)phenylacetate,
2-(2-propynylthio)ethyl 2-nitro-5-(2'-chloro-4'-trifluoromethylphenoxy)phenylacetate,
S-methoxymethyl 2-nitro-5-(2'-chloro-4'-trifluoromethylphenoxy)phenylthioacetate,
S-ethoxymethyl 2-nitro-5-(2'-chloro-4'-trifluoromethylphenoxy)phenylthioacetate,
S-2-methoxyethyl 2-nitro-5-(2'-chloro-4'-trifluoromethylphenoxy)phenylthioacetate,
S-2-ethoxyethyl 2-nitro-5-(2'-chloro-4'-trifluoromethylphenoxy)phenylthioacetate,
S-2-(2-propenyloxy)ethyl 2-nitro-5-(2'-chloro-4'-trifluoromethylphenoxy)phenylthioacetate,
S-3-methoxypropyl 2-nitro-5-(2'-chloro-4'-trifluoromethylphenoxy)phenylthioacetate,
S-1-methyl-2-methoxyethyl 2-nitro-5-(2'-chloro-4'-trifluoromethylphenoxy)phenylthioacetate,
S-2-methylthioethyl 2-nitro-5-(2'-chloro-4'-trifluoromethylphenoxy)phenylthioacetate,
2,2,2-trifluoroethyl 2-nitro-5-(2'-chloro-4'-trifluoromethylphenoxy)phenylacetate,
2-chloro-2-propenyl 2-nitro-5-(2'-chloro-4'-trifluoromethylphenoxy)phenylacetate,
carboxymethyl 2-nitro-5-(2'-chloro-4'-trifluoromethylphenoxy)phenylacetate,
1-carboxyethyl 2-nitro-5-(2'-chloro-4'-trifluoromethylphenoxy)phenylacetate,
methoxycarbonylmethyl 2-nitro-5-(2'-chloro-4'-trifluoromethylphenoxy)phenylacetate,
ethoxycarbonylmethyl 2-nitro-5-(2'-chloro-4'-trifluoromethylphenoxy)phenylacetate,
2-isopropoxycarbonylethyl 2-nitro-5-(2'-chloro-4'-trifluoromethylphenoxy)phenylacetate,
S-ethoxycarbonylmethyl 2-nitro-5-(2'-chloro-4'-trifluoromethylphenoxy)phenylthioacetate,
2-ethoxycarbonylethyl 2-nitro-5-(2'-chloro-4'-trifluoromethylphenoxy)phenylacetate,
1-methoxycarbonylethyl 2-nitro-5-(2'-chloro-4'-trifluoromethylphenoxy)phenylacetate,
1-ethoxycarbonylethyl 2-nitro-5-(2'-chloro-4'-trifluoromethylphenoxy)phenylacetate,
S-1-isopropoxycarbonylethyl 2-nitro-5-(2'-chloro-4'-trifluoromethylphenoxy)phenylthioacetate,
2-chloroethoxycarbonylmethyl 2-nitro-5-(2'-chloro-4'-trifluoromethylphenoxy)phenylacetate,
1-(2-bromoethoxycarbonyl)ethyl 2-nitro-5-(2'-chloro-4'-trifluoromethylphenoxy)phenylacetate,
1-cyanomethoxycarbonylethyl 2-nitro-5-(2'-chloro-4'-trifluoromethylphenoxy)phenylacetate,
1-(2-methoxyethoxycarbonyl)ethyl 2-nitro-5-(2'-chloro-4'-trifluoromethylphenoxy)phenylacetate,
S-2-ethoxyethoxycarbonylmethyl 2-nitro-5-(2'-chloro-4'-trifluoromethylphenoxy)phenylthioacetate,
1-(2-allyloxyethoxycarbonyl)ethyl 2-nitro-5-(2'-chloro-4'-trifluoromethylphenoxy)phenylacetate,
2-(2-propargyloxyethoxycarbonyl)ethyl 2-nitro-5-(2'-chloro-4'-trifluoromethylphenoxy)phenylacetate,
2-methylthioethoxycarbonylmethyl 2-nitro-5-(2'-chloro-4'-trifluoromethylphenoxy)phenylacetate, 2-allylthioethoxycarbonylmethyl 2-nitro-5-(2'-chloro-4'-trifluoromethylphenoxy)phenylacetate,
1-(2-propargylthioethoxycarbonyl)ethyl 2-nitro-5-(2',6'-dichloro-4'-trifluoromethylphenoxy)phenylacetate,
2-(2-hydroxyethoxycarbonyl)ethyl 2-nitro-5-(2'-chloro-4'-trifluoromethylphenoxy)phenylacetate,
1-acetylmethoxycarbonylethyl 2-nitro-5-(2'-chloro-4'-trifluoromethylphenoxy)phenylacetate,
1-(2-acetoxyethoxycarbonyl)ethyl 2-nitro-5-(2'-chloro-4'-trifluoromethylphenoxy)phenylacetate,
2-[2-nitro-5-(2'-chloro-4'-trifluoromethylphenoxy)-phenylacetoxyacetoxy]propionic acid,
carboxylmethyl 2-[2-nitro-5-(2'-chloro-4'-trifluoromethylphenoxy)phenylacetoxy]propionate,
methoxycarbonylmethyl 2-[2-nitro-5-(2'-chloro-4'-trifluoromethylphenoxy)phenylacetoxy]propionate,
ethoxycarbonylmethyl 2-[2-nitro-5-(2'-chloro-4'-trifluoromethylphenoxy)phenylacetoxy]propionate,
2-methoxyethyl 2-nitro-5-(2'-chloro-4'-trifluoromethylphenoxy)phenylacetoxyacetoxyacetate,
aminocarbonylmethyl 2-[2-nitro-5-(2'-chloro-4'-trifluoromethylphenoxy)phenylacetoxy]propionate,
1-allyloxycarbonylethyl 2-nitro-5-(2'-chloro-4'-trifluoromethylphenoxy)phenylacetate,
S-propargyloxycarbonylmethyl 2-nitro-5-(2'-chloro-4'-trifluoromethylphenoxy)phenylthioacetate,
2-chloropropenyloxycarbonylmethyl 2-nitro-5-(2'-chloro-4'-trifluoromethylphenoxy)phenylacetate,
sodium 2-nitro-5-(2'-chloro-4'-trifluoromethylphenoxy)phenylacetoxyacetate,
potassium 2-nitro-5-(2'-chloro-4'-trifluoromethylphenoxy)phenylacetylthioacetate,
sodium 2-[2-nitro-5-(2'-chloro-4'-trifluoromethylphenoxy)phenylacetoxy]propionate,
ammonium 2-nitro-5-(2'-chloro-4'-trifluoromethylphenoxy)phenylacetoxyacetate,
aminocarbomethyl 2-nitro-5-(2'-chloro-4'-trifluoromethylphenoxy)phenylacetate,
N-methyl-N-methoxy-2-nitro-5-(2'-chloro-4'-trifluoromethylphenoxy)phenylacetoxyacetamide,
N-methyl-2-[2-nitro-5-(2'-chloro-4'-trifluoromethylphenoxy)phenylacetoxy]propionamide,
N,N-dimethyl-2-[2-nitro-5-(2'-chloro-4'-trifluoromethylphenoxy)phenylacetoxy]propionamide,
N-methyl-3-[2-nitro-5-(2'-chloro-4'-trifluoromethylphenoxy)phenylacetoxy]propionamide,
sodium 2-[2-nitro-5-(2'-chloro-4'-trifluoromethylphenoxy)phenylacetoxy]propionyloxyacetate,
3-methoxycarbonylpropyl 2-nitro-5-(2'-chloro-4'-trifluoromethylphenoxy)phenylacetate,
1-methyl-1-ethoxycarbonylethyl 2-nitro-5-(2'-chloro-4'-trifluoromethylphenoxy)phenylacetate,
2-methyl-3-methoxycarbonylpropyl 2-nitro-5-(2'-chloro-4'-trifluoromethylphenoxy)phenylacetate,
2-nitro-5-(2'-chloro-4'-trifluoromethylphenoxy)-phenylacetamide,
N-methyl-2-nitro-5-(2'-chloro-4'-trifluoromethylphenoxy)phenylacetamide,
N-n-butyl-2-nitro-5-(2'-chloro-4'-trifluoromethylphenoxy)phenylacetamide,
N-iso-propyl-2-nitro-5-(2'-chloro-4'-trifluoromethylphenoxy)phenylacetamide,
N-(2-chloroethyl)-2'-nitro-5'-(2''-chloro-4'''-trifluoromethylphenoxy)phenylacetamide,
N-(2-hydroxybutyl)-2'-nitro-5'-(2''-chloro-4'''-trifluoromethylphenoxy)phenylacetamide,
N-methoxymethyl-2-nitro-5-(2'-chloro-4'-trifluoromethylphenoxy)phenylacetamide,
N-(2-cyanoethyl)-2'-nitro-5'-(2''-chloro-4'''-trifluoromethylphenoxy)phenylacetamide,
N-allyl-2-nitro-5-(2'-chloro-4'-trifluoromethylphenoxy)phenylacetamide,
N-(3-chloro-2-propenyl)-2'-nitro-5'-(2''-chloro-4'''-trifluoromethylphenoxy)phenylacetamide,
N-(2-propynyl)-2'-nitro-5'-(2''-chloro-4'''-trifluoromethylphenoxy)phenylacetamide,
N-(4-chlorobenzyl)-2'-nitro-5'-(2''-chloro-4'''-trifluoromethylphenoxy)phenylacetamide,
N-α,α-dimethylbenzyl-2-nitro-5-(2'-chloro-4'-trifluoromethylphenoxy)phenylacetamide,
N-(3,4-dichlorophenyl)-2'-nitro-5'-(2''-chloro-4'''-trifluoromethylphenoxy)phenylacetamide,
N-(4-methylphenyl)-2'-nitro-5'-(2''-chloro-4'''-trifluoromethylphenoxy)phenylacetamide,
N-α-naphtyl-2-nitro-5-(2'-chloro-4'-trifluoromethylphenoxy)phenylacetamide,
N,N-dimethyl-2-nitro-5-(2'-chloro-4'-trifluoromethylphenoxy)phenylacetamide,
N-methyl-N-phenyl-2-nitro-5-(2'-chloro-4'-trifluoromethylphenoxy)phenylacetamide,
N-(2-cyanoethyl)-N-phenyl-2'-nitro-5'-(2''-chloro-4'''-trifluoromethylphenoxy)phenylacetamide,
N-iso-butyl-2-nitro-5-(2'-chloro-4'-trifluoromethylphenoxy)phenylacetamide,
N-n-nonyl-2-nitro-5-(2'-chloro-4'-trifluoromethylphenoxy)phenylacetamide,
N-(2-hydroxyethyl)-2'-nitro-5'-(2''-chloro-4'''-trifluoromethylphenoxy)phenylacetamide,
N-n-butoxymethyl-2-nitro-5-(2'-chloro-4'-trifluoromethylphenoxy)phenylacetamide,
N-(2-n-propoxyethyl)-2'-nitro-5'-(2''-chloro-4'''-trifluoromethylphenoxy)phenylacetamide,
N-(2-methoxypropyl)-2'-nitro-5'-(2''-chloro-4'''-trifluoromethylphenoxy)phenylacetamide,
N-(2-bromoethyl)-2'-nitro-5'-(2''-chloro-4'''-trifluoromethylphenoxy)phenylacetamide,
N-α-ethoxycarbonylbenzyl-2-nitro-5-(2'-chloro-4'-trifluoromethylphenoxy)phenylacetamide,
N-cyanomethyl-2-nitro-5-(2'-chloro-4'-trifluoromethylphenoxy)phenylacetamide,
N-methyl-N-methoxy-2-nitro-5-(2'-chloro-4'-trifluoromethylphenoxy)phenylacetamide,
N-ethyl-N-n-propoxy-2-nitro-5-(2'-chloro-4'-trifluoromethylphenoxy)phenylacetamide,
N-allyl-N-methoxy-2-nitro-5-(2'-chloro-4'-trifluoromethylphenoxy)phenylacetamide,
N-ethyl-N-allyloxy-2-nitro-5-(2'-chloro-4'-trifluoromethylphenoxy)phenylacetamide,
N-n-propyl-N-propargyloxy-2-nitro-5-(2'-chloro-4'-trifluoromethylphenoxy)phenylacetamide,
N-methyl-N-ethoxycarbonylmethoxy-2-nitro-5-(2'-chloro-4'-trifluoromethylphenoxy)phenylacetamide,
N-methyl-N-(2-cyanoethoxy)-2'-nitro-5'-(2''-chloro-4'''-trifluoromethylphenoxy)phenylacetamide,
N,N-diallyl-2-nitro-5-(2'-chloro-4'-trifluoromethylphenoxy)phenylacetamide,
N-(2,2-diethoxyethyl)-2'-nitro-5'-(2''-chloro-4'''-trifluoromethylphenoxy)phenylacetamide,
N-(2-ethoxyethyl)-2'-nitro-5'-(2''-chloro-4'''-trifluoromethylphenoxy)phenylacetamide,
N-(4-methoxy-2-butenyl)-2'-nitro-5'-(2''-chloro-4'''-trifluoromethylphenoxy)phenylacetamide,
N-methyl-N-(3-chloro-2-propenyloxy)-2'-nitro-5'-(2''-chloro-4'''-trifluoromethylphenoxy)phenylacetamide, N-ethyl-N-(2-methoxycarbonylethoxy)-2'-nitro-5'-(2''-chloro-4'''-trifluoromethylphenoxy)phenylacetamide,
N-methyl-N-(2-chloroethoxy)-2'-nitro-5'-(2''-chloro-4''-trifluoromethylphenoxy)phenylacetamide,
N-(2-methylthioethyl)-2'-nitro-5'-(2''-chloro-4'''-trifluoromethylphenoxy)phenylacetamide,
N-(2-benzylthioethyl)-2'-nitro-5'-(2''-chloro-4'''-trifluoromethylphenoxy)phenylacetamide,
N-(2-allylthioethyl)-2'-nitro-5'-(2''-chloro-4''-trifluoromethylphenoxy)phenylacetamide,
N-methyl-N-(2-methylthioethoxy)-2'-nitro-5'-(2''-chloro-4'''-trifluoromethylphenoxy)phenylacetamide,
N-methyl-N-(4-methylmercaptophenyl)-2'-nitro-5'-(2''-chloro-4'''-trifluoromethylphenoxy)phenylacetamide,
N-methyl-N-(4-allylmercaptobenzyl)-2'-nitro-5'-(2''-chloro-4'''-trifluoromethylphenoxy)phenylacetamide,
N-ethyl-N-ethoxy-2-nitro-5-(2'-chloro-4'-trifluoromethylphenoxy)phenylacetamide,
N-ethyl-N-methoxy-2-nitro-5-(2'-chloro-4'-trifluoromethylphenoxy)phenylacetamide, and the like.

All of the above compounds are novel compounds which have not been disclosed in any literature. They may be prepared according to, for example, Method A and Method B as described below.

Method A

In another aspect of the present invention, there is provided a process for preparing a compound represented by the formula

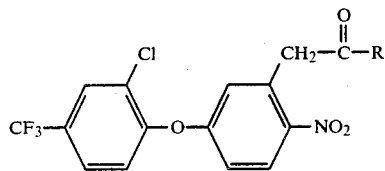 (I)

wherein
R is as defined above,
which comprises the steps of:
(1) heating potassium m-hydroxyphenylacetate and 3-chloro-4-halogenobenzotrifluoride at a temperature of from 90° to 180° C. to obtain 3-(2'-chloro-4'-trifluoromethylphenoxy)phenylacetic acid;
(2) reacting the acid with at least one member selected from the class consisting of an alcohol, an amine, a mercaptane and a halide compound which each have a substituent group of the formula R as defined above to obtain a compound represented by the formula

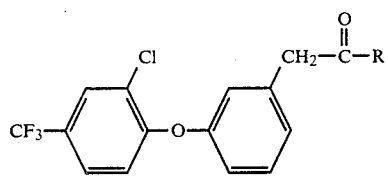 (II)

in which
R is as defined above; and
(3) nitrating the compound represented by the formula (II).

In step (1) above, the reaction may be conducted in a solvent such as dimethylsulfoxide. It is preferred that the reaction be conducted at a temperature of 90° to 180° C., especially 120° to 150° C. The yield of 3-(2'-chloro-4'-trifluoromethylphenoxy)phenylacetic acid may be improved by addition of potassium carbonate. In step (2) above, dehydration, desalting or the like may occur by the reaction of the acid with an alcohol, an amine, a mercaptane or a halide compound. In step (3) above, the compound of formula (II) may be nitrated using a customary nitrating agent such as acetyl nitrate, potassium nitrate in sulfuric acid, mixed acid of sulfuric acid and nitric acid and nitrosonium tetrafluoroborate to obtain a compound of formula (I) according to the present invention. The nitration may be conducted at a temperature of generally from about −20° C. to about 100° C., preferably from about −10° C. to about 50° C. According to need, the nitration may be conducted in an inert organic solvent such as 1,2-dichloroethane and other chlorohydrocarbons.

Method B

In a further aspect of the present invention, there is provided a process for preparing the compound of formula (I), which comprises reacting a 2-chloro-4-trifluoromethylphenol compound represented by the formula

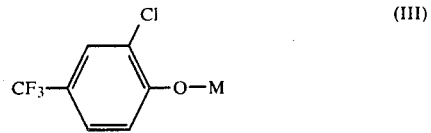 (III)

in which
M represents an alkali metal, with a 2-nitro-4-halogenophenylacetic acid compound or 2-nitro-4-halogenophenylthioacetic acid compound represented by the formula

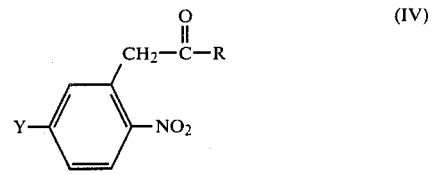 (IV)

in which
R is as defined above and Y represents a halogen group.

It is preferred that Y be a bromine atom or a fluorine atom. A fluorine atom is more preferred than a bromine atom.

As illustrated above, an alkali metal salt of 2-chloro-4-trifluoromethylphenol represented by the formula (III) and a derivative of phenylacetic acid or phenylthioacetic acid represented by the formula (IV) may be reacted to obtain a compound according to the present invention. This reaction may be conducted at a temperature of generally from 0° to 250° C., preferably from about 60° to 180° C. This reaction according to need, may be performed in a suitable solvent selected from sulfolane, dimethyl sulfoxide, N,N-dimethylformamide, hexamethylphosphorus triamide and other inert organic solvents.

The above Methods A and B are illustrative of preferred processes of the present invention. It should be understood that these methods are not intended to limit the present invention. The compounds of the present invention may be produced by various methods which are modifications of conventionally known methods for producing similar compounds.

The herbicidal activity of the compound of the present invention is illustrated hereinbelow with respect to the prevention and elimination of the weeds which grow on paddy fields. The compound of the present invention can be effectively applied to paddy fields in a prolonged period of time including the pre-transplantation and post-transplantation periods of rice plant seedlings. Especially, the compound is useful to effectively and promptly destroy barnyardgrass which is a hazardous weed of Gramineae family growing on paddy fields. Moreover, the compound of the present invention has no significant phytotoxicity to rice plants when it is applied in an effective amount such that the weeds are destroyed effectively. Further, the compound of the present invention also exhibits excellent herbicidal activities to broad-leaved weeds growing on paddy fields, such as monochoria, rotala spp, waterwort and false pimpernel. It is noted that the dosage of the compound of the present invention can be advantageously lower than those of the conventional herbicides. The esters and thioesters according to the present invention exhibits excellent herbicidal activities on paddy fields in a dosage of generally from 0.5 to 100 g/10 a, preferably from 1.5 to 50 g/10 a. The amides according to the present invention exhibits excellent herbicidal activities on paddy fields in a dosage of generally from 1 to 100 g/10 a, preferably from 5 to 50 g/10 a. These amounts are surprisingly low as compared with the dosage of from 200 to 250 g/10 a which is usually employed for the conventional paddy field herbicides such as 2,4,6-trichloro-1-(4'-nitrophenoxy)benzene, 2,4-dichloro-1-(3'-methoxy-4'-nitrophenoxy)benzene and methyl 2-nitro-5-(2',4'-dichlorophenoxy)benzoate. From the foregoing, it is apparent that the compound of the present invention has advantageously higher herbicidal activities than those of the conventional herbicides.

Further, the compound of the present invention exhibits extremely high herbicidal activities not only to the paddy field weeds but also to the upland weeds.

That is, the compound of the present invention exhibits high herbicidal activities, even in a small dosage, to a variety of weeds, for example, the broad-leaved weeds such as lambsquarters, velvetleaf, coffeeweed, tall morningglory, common purslane, prickly sida, sicklepod, jimsonweed, black nightshade, smartweed, common cocklebur, peppergrass, Marestail, Climbing milkweed, chickweed, bindweed, and the like, and the weeds belonging to the family Gramineae such as large crabgrass, goosegrass, green foxtail, annual bluegrass and the like. It is especially noted that the compound of the present invention exhibits high herbicidal activities in a small dosage to such troublesome weeds on soybean fields as velvetleaf, jimsonweed, prickly sida, lambsquarters and the like. The characteristic feature of the compound of the present invention resides in that it exhibits a high selectivity not only for broad-leaved crop plants such as soybean and cotton, but also for crop plants belonging to the family Gramineae such as rice, Indian corn, wheat and the like, in both the pre- and post-emergence applications. Due to its wide applicability and excellent herbicidal activities, the compound of the present invention is also useful as an effective herbicide for a pasture, an orchard, a lawn and a noncropland.

Methyl 2-nitro-5-(2'-chloro-4'-trifluoromethylphenoxy)phenyl acetate, which is a known compound having a structure similar to that of the compound of the present invention, has such a defect that it exhibits no genus selectivity between the rice plant and the barnyard grass. On the other hand, unlike the conventional diphenyl ether herbicides, the compound of the present invention exhibits, in addition to the excellent herbicidal activity, an extremely high genus selectivity among the plants belonging to the family Gramineae. Accordingly, it can be stated that the compound of the present invention provides an extremely effective, useful herbicide.

As is apparent from the foregoing, the compound of the present invention can be utilized for selective destruction of weeds growing among plants of rice, cereals such as barley and wheat, Indian corn, soybean and cotton. Further, the compound of the present invention can be utilized in both the pre- and post-emergence applications.

The compound of the present invention can be applied in a wide range of dosage depending on the method of application of the compound, the location of application of the compound and the kind of weed to be destroyed. For example, the esters and thioesters according to the present invention may be applied in an amount of from 0.5 to 100 g/10 a, preferably from 1.5 to 50 g/10 a. The amides according to the present invention may be applied in an amount of from 1 to 100 g/10 a, preferably from 5 to 50 g/10 a.

In practical application of the present compound as a herbicide, it may be applied as such, or may be formulated into various types of preparations, such as wettable powder, emulsifiable concentrate, granule, dust and the like. Hence, in a still further aspect of the present invention, there is provided a herbicidal composition which comprises, together with an agriculturally acceptable carrier, as an active ingredient a herbicidally effective amount of a compound represented by the formula

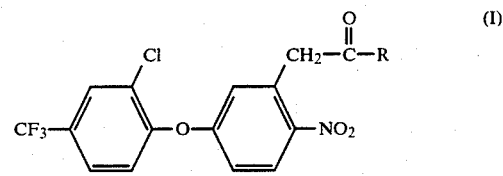

wherein
R is as defined above.

As the solid carrier to be used for formulating the present compound into the above-described various preparations, there may be mentioned mineral powder (e.g. kaolin, bentonite, clay, montmorillonite, talc, diatomite, mica, vermiculite, gypsum, calcium carbonate, apatite and the like), vegetable powder (e.g. soybean meal, wheat flour, wood meal, tobacco powder, starch, crystalline cellulose and the like), high polymer compounds (e.g. petroleum resin, polyvinyl chloride, ketone resin and the like) and, further, alumina and waxes. As the liquid carrier, there may be mentioned for example, alcohols (methanol, ethanol, butanol, ethylene glycol, benzyl alcohol and the like), aromatic hydrocarbons (such as toluene, benzene, xylene and the like), chlorinated hydrocarbons (chloroform, carbon tetrachloride, monochlorobenzene and the like), ethers (dioxane, tetrahydrofuran and the like), ketones (acetone, methyl ethyl ketone, cyclohexanone and the like), esters (ethyl acetate, butyl acetate and the like), acid amides (N,N-dimethylacetamide and the like), nitriles (acetonitrile and the like), ether alcohols (ethylene glycol ethyl ether and the like) and water.

As the surface active agent to be used to effect emulsifying, dispersing, spreading and the like for the present compound, there may be mentioned non-ionic, anionic, cationic and amphoteric ones. Specific examples of the surface active agent which can be employed in the present invention are a polyoxyethylene alkyl ether, a polyoxyethylene alkylaryl ether, a polyoxyethylene fatty acid ester, a sorbitan fatty acid ester, a polyoxyethylene sorbitan fatty acid ester, an oxyethylene polymer, an oxypropylene polymer, a polyoxyethylene alkyl phosphate, a fatty acid salt, an alkyl sulfate salt, an alkyl sulfonate salt, an alkyl aryl sulfonate salt, an alkyl phosphate salt, a polyoxyethylene alkyl sulfate, a quaternary ammonium salt and an oxyalkylamine. It should be noted that the surface active agents which can be employed in the present invention are not limited to the above-cited compounds. Further according to need, gelatin, casein, sodium alginate, starch, agar, polyvinyl alcohol and the like may be used as an auxiliary additive in the present invention.

Moreover, in order to improve the effect as a herbicide, the compound of the present invention may be mixed with other herbicidally active ingredients and, in some cases, a synergistic effect is expectable. For example, the following ingredients may be mixed with the compound of the present invention.

(A) Phenoxy type herbicide 2,4-dichlorophenoxyacetic acid; 2-methyl-4-chlorophenoxyacetic acid; butyl 2-[4-(5-trifluoromethyl-2-pyridyloxy)phenoxy]propionate (including esters and salts thereof); ethyl 2-[4-(6-chloro-2-quinoxalinyloxy)-phenoxy]propionate; etc.

(B) Diphenyl ether type herbicide 2,4-dichlorophenyl 4'-nitrophenyl ether; 2,4,6-trichlorophenyl 4'-nitrophenyl ether; 2,4-dichlorophenyl 4'-nitro-3'-methoxyphenyl ether; 2,4-dichlorophenyl 3'-methoxycarbonyl-4'-nitrophenyl ether; 2-chloro-4-trifluoromethylphenyl 3'-ethoxy-4'-nitrophenyl ether; sodium 5-[2-chloro-4-(trifluoromethyl)phenoxy]-2-nitrobenzoate; etc.

(C) Triazine type herbicide 2-chloro-4,6-bis-ethylamino-1,3,5-triazine; 2-chloro-4-ethylamino-6-isopropylamino-1,3,5-triazine; 2-methylthio-4,6-bis-ethylamino-1,3,5,-triazine; etc.

(D) Urea type herbicide 3-(3,4-dichlorophenyl)-1,1-dimethylurea; 3-(3,4-dichlorophenyl)-1-methoxy-1-methylurea; 3-(α,α,α-trifluoro-m-tolyl)-1,1-dimethylurea; 3-[4-(4-methylphenethyloxy)phenyl]-1- methoxy-1- methylurea; 3-(5-t-butyl-3,4-thiadiazol-2-yl)-4-hydroxy-1-methyl-2-imidazolidone; etc.

(E) Carbamate type herbicide isopropyl N-(3-chlorophenyl)carbamate; methyl N-(3,4-dichlorophenyl)carbamate; 4-chloro-2-butynyl N-(3-chlorophenyl)carbamate; etc.

(F) Thiolcarbamate type herbicide

S-ethyl N,N-hexamethylenethiolcarbamate; S-(4-chlorobenzyl) N,N-diethylthiolcarbamate; S-ethyl dipropylthiolcarbamate; etc.

(G) Anilide type herbicide 3,4-dichloropropionanilide; N-methoxymethyl-2',6'-diethyl-2-chloroacetanilide; 2-chloro-2',6'-diethyl-N-(butoxymethyl)-acetanilide; 2-chloro-2',6'-diethyl-N-(propoxyethyl)-acetanilide; α-(2-naphthoxy)propionanilide; etc.

(H) Uracil type herbicide 5-bromo-3-sec-butyl-6-methyluracil; 3-cyclohexyl-5,6-trimethyleneuracil; etc.

(I) Dipyridinium salt type herbicide
1,1'-dimethyl-4,4'-dipyridinium dichloride; 1,1'-ethylene-2,2'-dipydinium dibromide; etc.

(J) Phosphorus type herbicide

N-(phosphonomethyl)glycine; O-ethyl,O-(2-nitro-5-methylphenyl) N-sec-butylphosphoroamidothioate; O-methyl, O-(2-nitro-4-methylphenyl)N-isopropylphosphoroamidothioate; S-(2-methyl-1,1-piperidylcarbonylmethyl) O,O-di-n-propyl dithiophosphate; (2-amino-4-methylphosphinobutyryl)alanylalanine monosodium salt; etc.

(K) Toluidine type herbicide

α,α,α-trifluoro-2,6-dinitro-N,N-dipropyl-p-toluidine; N-(cyclopropylmethyl)-α,α,α-trifluoro-2,6-dinitro-N-propyl-p-toluidine; etc.

(L) Other herbicides 5-t-butyl-3-(2,4-dichloro-5-isopropoxyphenyl)-1,3,4-oxadiazolin-2-one; 3-isopropyl-2,1,3-benzothiaziadinone-4,2,2-dioxide; 2-(α-naphthoxy)-N,N-diethylpropionamide; 3-amino-2,5-dichlorobenzoic acid; 4-(2,4-dichlorobenzoyl)-1,3-dimethylpyrazol-5-yl-p-toluene sulfonate; 2-chloro-N-[(4-methoxy-6-methyl-1,3,5-triazine-2-yl)aminocarbonyl]benzenesulfonamide; methyl 2-[(4,6-dimethoxypyrimidin-2-yl)aminocarbonylaminosulfonylmethyl]benzoate; N-(1-methyl-1-phenylethyl)-2-bromo-3,3-dimethylbutanamide; 2-[1-(N-allyloxyamino)butylidene]-4-methoxycarbonyl-5,5-dimethylcylohexane-1,3-dione sodium salt; 2-[1-(ethoxyimino)butyl]-5-(2-ethylthiopropyl)-3-hydroxy-2-cyclohexan-1-one; etc.

The foregoing herbicides are mentioned only as the examples, and they should not be construed to be limiting the scope of herbicides which can be utilized in combination with the compound of the present invention. The herbicide of the present invention may also be applied in combination with insecticides such as pyrethroid type insecticides, fungicides, plant growth regulators, microbial agricultural chemicals and fertilizers.

In an additional aspect of the present invention, there is provided a method for the destruction of undesirable weeds, which comprises applying to said weeds a herbicidally effective amount of a compound represented by the formula

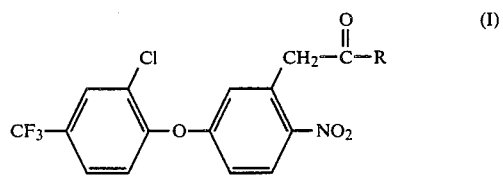

wherein

R is as defined above, as such or in the form of a herbicidal composition comprising said compound as an active ingredient and an agriculturally acceptable carrier as defined above. The meaning of the above-mentioned "herbicidally effective amount" is apparent from the foregoing description. The dosage of the esters and thioesters according to the present invention may be in the range of from 0.5 to 100 g/10 a, preferably from 1.5 to 50 g/10 a. On the other hand, the dosage of the amides according to the present invention may be in the range of from 1 to 100 g/10 a, preferably from 5 to 50 g/10 a. The above-described method is useful in selectively controlling undesirable weeds among desirable crop plants. In Application Examples which will be given later and in which the active compound is applied in the form of a herbicidal composition, the dosage of the composition is expressed using the unit "a.i. g/10 a" which means "g/10 a in terms of the amount of an active compound".

EXAMPLE

The present invention will now be explained in more detail with reference to Examples with respect to the preparation of the compound of the present invention and Application Examples with respect to the recipes and effectiveness of the compound of the present invention as a herbicide. These Examples are not to be construed as limiting the scope of the invention in any manner.

EXAMPLE 1

Preparation of S-ethyl 2-nitro-5-(2'-chloro-4'-trifluoromethylphenoxy)phenylthioacetate: Compound No. 2

(a) 0.7 g of ethyl mercaptan and 1.2 g of triethylamine were dissolved in 20 ml of N,N-dimethylacetamide. To the resulting solution, 3.5 g of 3-(2'-chloro 4'-trifluoromethylphenoxy)phenylacetyl chloride was dropwise added at 10° C. After completion of the dropwise addition, the reaction was allowed to proceed at room temperature for 3 hours. After completion of the reaction, 50 ml of water was added to the liquid reaction mixture, followed by extraction twice with 30 ml portions of ether. The ether layer was washed with water and dried over anhydrous sodium sulfate, followed by evaporation-removal of the ether under reduced pressure, thereby to obtain a crude product. The so-obtained crude product was subjected to purification by the silica gel column chromatography (elution was performed by using a mixed solvent of toluene and n-hexane). As a result, there was obtained 1.9 g of S-ethyl 3-(2'-chloro-4'-trifluoromethylphenoxy)phenylthioacetate.

(b) 1.9 g of S-ethyl 3-(2'-chloro-4'-trifluoromethylphenoxy)phenylthioacetate as obtained in step (a) above was added to 15 g of acetic anhydride, and the mixture was cooled to below 10° C. on the ice bath while stirring. Subsequently, 1.5 g of copper nitrate was gradually added over a period of 5 minutes. After completion of the addition, the reaction was allowed to proceed at below 10° C. for 1 hour and then at room temperature for further 3 hours. The reaction mixture was poured onto ice, followed by addition of 200 ml of ether. The resulting mixture was neutralized by addition of an aqueous sodium hydroxide solution. The mixture was then acidified with an aqueous hydrochloric acid solution, and the ether extract layer was separated, washed with water and dried over anhydrous sodium sulfate, followed by evaporation-removal of the ether under reduced pressure to obtain a crude crystal product. The so-obtained crude product was subjected to purification by the silica gel column chromatography (elution was performed by using a mixed solvent of toluene and acetone). As a result, there was obtained 1.1 g of a light yellow solid substance of S-ethyl 2-nitro-5-(2'-chloro-4'-trifluoromethylphenoxy)phenylthioacetate having a melting point of 82.5° to 84.2° C.

EXAMPLE 2

Preparation of S-1-methylethyl 2-nitro-5-(2'-chloro-4'-trifluoromethylphenoxy)phenylthioacetate: Compound No. 3

(a) 3.3 g of 3-(2'-chloro-4'-trifluoromethylphenoxy)phenylacetic acid was dissolved in 30 ml of dichloromethane, and the resulting solution was cooled to below 10° C. on the water bath. Then, 2.1 g of N,N'-dicyclohexylcarbodiimide (DCC) was added, followed by addition of 0.8 g of 2-propanethiol. The reaction was allowed to proceed at room temperature for about 6 hours. After completion of the reaction, the formed solid substance was filtered off, and the filtrate was subjected to evaporation-removal of the solvent under reduced pressure to obtain a crude product. The thus obtained crude product was subjected to purification by the silica gel column chromatography (elution was performed by using a mixed solvent of toluene and n-hexane). As a result, there was obtained 1.6 g of S-1-methylethyl 3-(2'-chloro-4'-trifluoromethylphenoxy)phenylthioacetate.

(b) 1.6 g of S-1-methylethyl 3-(2'-chloro-4'-trifluromethylphenoxy)phenylthioacetate as obtained in step (a) above was added to 15 g of acetic anhydride, and the mixture was cooled to below 10° C. on the ice bath while stirring. Subsequently, 1.2 g of copper nitrate was gradually added over a period of 5 minutes. After completion of the addition, the reaction was allowed to proceed at below 10° C. for 1 hour and then at room temperature for further 3 hours to obtain the intended product. The intended product was isolated from the reaction mixture in substantially the same manner as in step (b) in Example 1. The so-obtained crude product was subjected to purification by the silica gel column chromatography (elution was performed by using a mixed solvent of toluene and acetone). As a result, there was obtained 1.1 g of a light yellow solid substance of S-1-methylethyl 2-nitro-5-(2'-chloro-4'-trifluoromethylphenoxy)phenylthioacetate having a melting point of 102° to 104° C.

EXAMPLE 3

Preparation of 2-methoxyethyl 2-nitro-5-(2'-chloro-4'-trifluoromethylphenoxy)phenylacetate: Compound No. 15

(a) 3.3 g of 3-(2'-chloro-4'-trifluoromethylphenoxy)phenylacetic acid and 1.5 g of 2-methoxyethanol were dissolved in 50 ml of benzene, followed by addition of 0.5 g of p-toluene sulfonic acid. Then, the mixture was heated under reflux for 3 hours. After completion of the reaction, to the reaction mixture was added 50 ml of ether. The resulting mixture was washed with water by the customary method and dried over anhydrous sodium sulfate, followed by evaporation-removal of the solvent under reduced pressure, thereby to obtain 3.9 g of 2-methoxyethyl 3-(2'-chloro-4'-trifluoromethylphenoxy)phenylacetate.

(b) 3.9 g of 2-methoxyethyl 3-(2'-chloro-4'-triflurome-thylphenoxy)phenylacetate as obtained in step (a) above was added to 35 g of acetic anhydride, and the mixture was cooled to below 10° C. on the ice bath while stirring. Subsequently, 2.9 g of copper nitrate was gradually added over a period of 5 minutes. After completion of the addition, the reaction was allowed to proceed at below 10° C. for 1 hour and then at room temperature for further 5 hours to complete the reaction. The reaction mixture was poured onto ice, followed by addition of 200 ml of ether. The resulting mixture was neutralized by addition of an aqueous sodium hydroxide solution. The mixture was then acidified with an aqueous hydrochloric acid solution, and the ether extract layer was separated, washed with water and dried over anhydrous sodium sulfate, followed by evaporation-removal of the ether under reduced pressure to obtain a crude crystal product. The thus obtained crude crystal product was subjected to recrystallization from a mixed solvent of ethyl acetate and n-hexane. As a result, there was obtained 3 g of a white crystal product of 2-methoxyethyl 2-nitro-5-(2'-chloro-4'-trifluoromethyl-phenoxy)phenylacetate having a melting point of 71.9° to 72.5° C.

EXAMPLE 4

I. Preparation of 1-methyl-2-methoxyethyl 2-nitro-5-(2'-chloro-4'-trifluoromethylphenoxy)phenylacetate: Compound No. 17

(a) 3.3 g of 3-(2'-chloro-4'-trifluoromethylphenoxy)-phenylacetic acid and 1.8 g of 1-methoxy-2-propanol were dissolved in 50 ml of benzene, followed by addition of 0.5 g of p-toluene sulfonic acid. Then, the mixture was heated under reflux for 6 hours. After completion of the reation, 50 ml of ether was added to the reaction mixture. The resulting mixture was washed with water by the customary method and dehydrated with anhydrous sodium sulfate, and the solvent was distilled off under reduced pressure to obtain 3.9 g of 1-methyl-2-methoxyethyl 3-(2'-chloro-4'-trifluoromethylphenoxy)phenylacetate.

(b) 3 g of 1-methyl-2-methoxyethyl 3-(2'-chloro-4'-trifluoromethylphenoxy)phenylacetate as obtained in step (a) above was dissolved in 15 g of 1,2-dichloroethane. The resulting solution was dropwise added to a mixed acid (2.4 g of 65% concentrated nitric acid and 3 g of 97% concentrated sulfuric acid) at 40° C. over a period of about 10 minutes. After completion of the addition, the reaction was allowed to proceed at 40° C. for 2.5 hours. After completion of the reaction, the reaction mixture was poured onto crushed ice, followed by extraction twice with 100 ml portions of ethyl acetate by the customary method. Then, the organic layer was washed with water and dried over anhydrous sodium sulfate, and the solvent was distilled off under reduced pressure to obtain a crude crystal product. The so-obtained crystal product was subjected to recrystallization from a mixed solvent of ethyl acetate and n-hexane to obtain 2.3 g of a white solid substance of 1-methyl-2-methoxyethyl 2-nitro-5-(2'-chloro-4'-trifluoromethylphenoxy)phenylacetate having a melting point of 78.9°–79.3° C. II. Preparation of 1-methyl-2-methoxyethyl 2-nitro-5-(2'-chloro-4'-trifluoromethylphenoxy)-phenylacetate: Compound No. 17

2.3 g of a potassium salt of 2-chloro-4-trifluoromethylphenol and 2.7 g of 1-methyl-2-methoxyethyl 2-nitro-5-fluorophenylacetate were dissolved in 50 ml of dimethyl solfoxide. The resulting solution was heated under reflux at 60°–70 ° C. for 5 hours. After completion of the reaction, the reaction mixture was poured into 300 ml of iced water, followed by extraction with ether. Then, the ether layer was washed with water and dried over anhydrous sodium sulfate, and the solvent was distilled off under reduced pressure to obtain crude crystals. The thus obtained crystals were subjected to recrystallization from a mixed solvent of ethyl acetate and n-hexane to obtain 3.2 g of a white solid substance of 1-methyl-2-methoxyethyl 2-nitro-5-(2'-chloro-4'-trifluoromethylphenoxy)phenylacetate having a melting point of 78.5°–79.0 ° C.

EXAMPLE 5

Preparation of methoxycarbonylmethyl 2-nitro-5-(2'-chloro-4'-trifluoromethylphenoxy)phenylacetate: Compound No. 37

(a) 3.3 g of 3-(2'-chloro-4'-trifluoromethylphenoxy) phenylacetic acid and 1 g of methylglycolate were dissolved in 50 ml of benzene. Then, 0.2 g of p-toluenesulfonic acid was added to the resulting solution, followed by heating under reflux for 3 hours. After completion of the reaction, 50 ml of ether was added. The resulting reaction mixture was washed with water according to the customary method and dehydrated with anhydrous sodium sulfate, and the solvent was distillend off under reduced pressure to obtain 3.4 g of methoxycarbonylmethyl 3-(2'-chloro-4'-trifluoromethylphenoxy)phenylacetate.

(b) 3.4 g of methoxycarbonylmethyl 3-(2'-chloro-4'-trifluoromethylphenoxy)phenylacetate as obtained in step (a) above was added to 35 g of anhydrous acetic acid and cooled to below 10° C. on an ice bath while stirring. Then, 2.4 g of copper nitrate was gradually added over a period of 5 minutes. After completion of the addition, the reaction was allowed to proceed at below 10° C. for 1 hour and then at room temperature for 5 hours to complete reaction. The liquid reaction mixture was placed on an ice bath and 200 ml of ether was added. The liquid reaction mixture was neutralized with an aqueous sodium hydroxide solution and then acidified with hydrochloric acid. The ether layer was separated, washed with water and dried over anhydrous sodium sulfate, and the ether was distilled off under reduced pressure to obtain a crude product. The obtained crude product was subjected to purification by the silica gel column chromatography. As a result, there was obtained 2.2 g of light yellow crystals of methoxycarbonylmethyl 2-nitro-5-(2'-chloro-4'-trifluoromethylphenoxy)phenylacetate having a melting point of 79.2° to 80.1° C.

EXAMPLE 6

Preparation of S-ethoxycarbonylmethyl 2-nitro-5-(2'-chloro-4'-trifluoromethylphenoxy)phenyl-thioacetate Compound No. 47

(a) 1.2 g of ethyl thioglycolate and 1.2 g of triethylamine were dissolved in 20 ml of N,N-dimethylacetamide. To the thus obtained solution was dropwise added 3.5 g of 3-(2'-chloro-4'-trifluoromethylphenoxy)-phenylacetyl chloride at 10° C. After completion of the dropwise addition, the reaction was allowed to proceed at room temperature for 3 hours to complete reaction.

After completion of the reaction, 50 ml of water was added to the reaction mixture, followed by extraction twice with 30 ml portions of ether. The ether layer was washed with water and dried over anhydrous sodium sulfate, and the ether was distilled off under reduced pressure to obtain a crude product. The obtained crude product was subjected to purification by the silica gel column chromatography to obtain 3.5 g of S-ethoxycarbonylmethyl 3-(2'-chloro-4'-trifluoromethylphenoxy)phenylthioacetate.

(b) 3.5 g of S-ethoxycarbonylmethyl 3-(2'-chloro-4'-trifluoromethylphenoxy)phenylthioacetate as obtained in step (a) above was added to 35 g of anhydrous acetic acid and cooled to below 10° C. on an ice bath while stirring. Subsequently, 2.3 g of copper nitrate was gradually added over a period of 5 minutes. After completion of the addition, reaction was allowed to proceed at below 10° C. for 1 hour and then at room temperature for 3 hours to complete reaction. Substantially the same procedures as described in step (b) of Example 1 were repeated to obtain a crude product. The so-obtained crude product was subjected to purification by the silica gel column chromatography. As a result, there was obtained 2.3 g of a light yellow oily substance of S-ethoxycarbonylmethyl 2-nitro-5-(2'-chloro-4'-trifluoromethylphenoxy)phenylthioacetate (refractive index $n_D^{26}$: 1.5578).

EXAMPLE 7

Preparation of 1-methoxycarbonylethyl 2-nitro-5-(2'-chloro-4'-trifluoromethylphenoxy)phenylacetate: Compound No. 48

(a) 3.3 g of 3-(2'-chloro-4'-trifluoromethylphenoxy)phenylacetic acid and 1.7 g of methyl α-bromopropionate were dissolved in 30 ml of acetone. Then, to the obtained solution was added 1.4 g of anhydrous potassium carbonate and stirred at room temperature for 30 minutes. Then, the reaction mixture was heated under reflux for 30 minutes. After completion of the reaction, the formed solid substance was filtered off and the acetone was distilled off under reduced pressure to obtain 4 g of 1-methoxycarbonylethyl 3-(2'-chloro-4'-trifluoromethylphenoxy)phenylacetate.

(b) 4 g of 1-methoxycarbonylethyl 3-(2'-chloro-4'-trifluoromethylphenoxy)phenylacetate as obtained in step (a) above was added to 35 g of anhydrous acetic acid and cooled to below 10° C. on an ice bath while stirring. Subsequently, 2.9 g of copper nitrate was added gradually over a period of 5 minutes. After completion of the addition, reaction was allowed to proceed at below 10° C. for 1 hour and then at room temperature for 3 hours to complete reaction. Substantially the same procudures as described in step (b) of Example 1 were repeated to obtain a crude product. The obtained crude product was recrystalized from a mixed solvent of ethyl acetate and n-hexane to obtain 3.1 g of white crystals of 1-methoxycarbonylethyl 2-nitro-5-(2'-chloro-4'-trifluoromethylphenoxy)phenylacetate having a melting point of 72.1° to 72.9 ° C.

EXAMPLE 8

Preparation of N-ethyl-2-nitro-5-(2'-chloro-4'-trifluoromethylphenoxy)phenylacetamide: Compound No. 59

(a) 0.7 g of ethylamine and 1.5 g of triethylamine were dissolved in 20 ml of N,N'-dimethylacetamide at 0° C., followed by addition of 3.5 g of 3-(2'-chloro-4'-trifluoromethylphenoxy)phenylacetyl chloride. The reaction was allowed to proceed at 0° C. for 1 hour and then at room temperature for further 3 hours to complete the reaction. After completion of the reaction, 50 ml of water was added to the liquid reaction mixture, followed by extraction twice with 30 ml portions of ether. The ether layer was washed with dilute hydrochloric acid and water and dried over anhydrous sodium sulfate, and the ether was distilled off under reduced pressure. As a result, there was obtained 3.5 g of N-ethyl-3-(2'-chloro-4'-trifluoromethylphenoxy)phenylacetamide.

(b) 3.5 g of N-ethyl-3-(2'-chloro-4'-trifluoromethylphenoxy)phenylacetamide as obtained in step (a) above was added to 35 g of acetic anhydride and cooled to below 10° C. on an ice bath while stirring. Then, 2.9 g of copper nitrate was gradually added over a period of 5 minutes. After completion of the addition, the reaction was allowed to proceed at below 10° C. for 1 hour and then at room temperature for further 5 hours to complete the reaction. Substantially the same procedures as described in step (b) of Example 1 were repeated to obtain crude crystals. The thus obtained crude crystals were subjected to recrystallization from a mixed solvent of ethyl acetate and n-hexane to obtain 2.5 g of white crystals of N-ethyl-2-nitro-5-(2'-chloro-4'-trifluoromethylphenoxy)phenylacetamide having a melting point of 188.7°–189.3° C.

EXAMPLE 9

Preparation of N-methyl-N-methoxy-2-nitro-5-(2'-chloro-4'-trifluoromethylphenoxy)phenylacetamide: Compound No. 90

(a) 0.9 g of N,O-dimethylhydroxylamine and 1.5 g of triethylamine were dissolved in 20 ml of N,N-dimethylacetamide at 5° C., followed by addition of 3.5 g of 3-(2'-chloro-4'-trifluoromethylphenoxy)phenylacetyl chloride. The reaction was allowed to proceed at 5° C. for 1 hour and then at room temperature for further 3 hours to complete the reaction. After completion of the reaction, 50 ml of water was added to the liquid reaction mixture, followed by extraction twice with 30 ml portions of ether. The ether layer was washed with dilute hydrochloric acid and water and dried over anhydrous sodium sulfate, and the ether was distilled off under reduced pressure to obtain 3.5 g of N-methyl-N-methoxy-2-nitro-5-(2'-chloro-4'-trifluoromethylphenoxy)phenylacetamide.

(b) 3.5 g of N-methyl-N-methoxy-2-nitro-5-(2'-chloro-4'-trifluoromethylphenoxy)phenylacetamide was added to 35 g of acetic anhydride, and the resulting mixture was cooled to below 10° C. on an ice bath while stirring. Then, 2.9 g of copper nitrate was gradually added to this mixture over a period of 5 minutes. After completion of the addition, the reaction was allowed to proceed at below 10° C. for 1 hour and then at room temperature for further 5 hours to complete the reaction. Substantially the same procedures as described in step (b) of Example 1 were repeated to obtain a crude crystal product. The thus obtained product was subjected to recrystallization from a mixed solvent of ethyl acetate and n-hexane to obtain 3.2 g of white crystals of N-methyl-N-methoxy-2-nitro-5-(2'-chloro-4'-trifluoromethylphenoxy)phenylacetamide having a melting point of 134°–135 ° C.

EXAMPLE 10

In substantially the same manner as in the above Examples, various compounds of the present invention were prepared. The structures, physical properties, elemental analysis results and $^1$H-NMR analysis data of these compounds are shown in Table 1. However, it should be understood that the scope of the present invention is by no means limited to these compounds. The numerals used to refer to the compounds listed Table 1 will also be used to designate the identical compounds in the Examples incorporated herein.

TABLE 1

Structure:

$$CF_3-\text{Ar}(Cl)-O-\text{Ar}(NO_2)-CH_2\overset{O}{\underset{\|}{C}}-X-R^8$$

| Compound No. | X | R$^8$ | Physical Properties | Calc. C | Calc. H | Calc. N | Found C | Found H | Found N | $^1$H—NMR Spectral Data (δ:CDCl$_3$) |
|---|---|---|---|---|---|---|---|---|---|---|
| 1 | S | —CH$_3$ | Viscous liquid* | 47.35 | 2.74 | 3.45 | 47.31 | 2.69 | 3.51 | 2.30(s, 3H), 4.20(s, 2H), 6.77~8.20(m, 6H) |
| 2 | S | —C$_2$H$_5$ | mp (°C.) 82.5~84.2 | 48.63 | 3.13 | 3.34 | 48.62 | 3.17 | 3.39 | 1.23(t, 3H), 2.87(q, 2H), 4.20(s, 2H), 6.73~8.23(m, 6H) |
| 3 | S | —CH(CH$_3$)CH$_3$ | mp (°C.) 102~104 | 49.83 | 3.49 | 3.23 | 49.91 | 3.50 | 3.29 | 1.27(d, 6H), 3.36~3.97(m, 1H), 4.16(s, 2H), 6.23~8.23(m, 6H) |
| 4 | S | —C$_4$H$_9$ | Viscous liquid* | 50.95 | 3.83 | 3.13 | 50.91 | 3.89 | 3.20 | 0.70~2.07(m, 7H), 2.90(t, 2H), 4.20(s, 2H), 6.80~8.27(m, 6H) |
| 5 | S | —CH$_2$CH=CH$_2$ | Viscous liquid* | 50.06 | 3.04 | 3.24 | 50.11 | 3.12 | 3.21 | 3.53(d, 2H), 4.20(s, 2H), 4.90~6.03 (m, 3H), 6.80~8.27(m, 6H) |
| 6 | S | cyclohexyl | mp (°C.) 97~99 | 53.22 | 4.05 | 2.96 | 53.00 | 4.13 | 2.89 | 0.70~2.07(m, 10H), 3.27~3.77(m, 1H), 4.23(s, 2H), 6.83~8.30(m, 6H) |
| 7 | S | phenyl | mp (°C.) 63.2~64.1 | 53.91 | 2.81 | 2.99 | 53.81 | 2.90 | 3.04 | 4.33(s, 2H), 6.86~8.37(m, 11H) |
| 8 | O | —CH$_2$CH=CH$_2$ | mp (°C.) 70.6~70.9 | 52.00 | 3.15 | 3.36 | 52.12 | 3.04 | 3.49 | 3.97(s, 2H), 4.56(d, 2H), 5.00~6.20 (m, 3H), 6.73~8.20(m, 6H) |
| 9 | O | —CH$_2$C≡CH | mp (°C.) 62.7~63.0 | 52.25 | 2.67 | 3.38 | 52.40 | 2.59 | 3.43 | 2.37~2.53(m, 1H), 4.00(s, 2H), 4.65(d, 2H), 6.73~8.27(m, 6H) |
| 10 | O | cyclohexyl | mp (°C.) 118.6~119.5 | 55.09 | 4.18 | 3.05 | 55.21 | 4.08 | 3.11 | 1.00~2.00(m, 10H), 3.94(s, 2H), 4.67(b, 1H), 6.76~8.23(m, 6H) |
| 11 | O | —CH$_2$-phenyl | Viscous liquid* | 56.72 | 3.24 | 3.00 | 56.59 | 3.16 | 2.82 | 3.94(s, 2H), 5.05(s, 2H), 6.70~8.16 (m, 6H), 7.23(s, 5H) |
| 12 | O | phenyl | Viscous liquid* | 55.82 | 2.90 | 3.10 | 55.95 | 2.76 | 3.02 | 4.13(s, 2H), 6.70~8.23(m, 11H) |
| 13 | O | —CH(CH$_3$)CH=CH$_2$ | mp (°C.) 96.5~97.5 | 53.09 | 3.51 | 3.25 | 53.18 | 3.42 | 3.50 | 1.31(d, 3H), 3.97(s, 2H), 4.95~6.23 (m, 4H), 6.72~8.35(m, 6H) |
| 14 | O | phenyl-COOCH$_3$ | mp (°C.) 100.2~101 | 48.06 | 3.36 | 3.11 | 48.24 | 3.41 | 3.03 | 3.84(s, 3H), 4.17(s, 2H), 6.71~8.30 (m, 10H) |
| 15 | O | —CH$_2$CH$_2$OCH$_3$ | mp (°C.) 71.9~72.5 | 49.84 | 3.49 | 3.23 | 49.82 | 3.55 | 3.30 | 3.36(s, 3H), 3.47~3.73(m, 2H), 4.03 (s, 2H), 4.16~4.33(m, 2H), 6.83~8.27(m, 6H) |

TABLE 1-continued

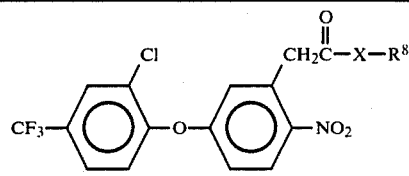

| Compound No. | X | R⁸ | Physical Properties | Elemental Analysis Calculated C | H | N | Found C | H | N | ¹H—NMR Spectral Data (δ:CDCl₃) |
|---|---|---|---|---|---|---|---|---|---|---|
| 16 | O | —CH₂CH₂OC₂H₅ | mp (°C.) 40.9~41.6 | 50.96 | 3.83 | 3.13 | 51.00 | 3.79 | 3.14 | 1.20(t, 3H), 3.33~3.80(m, 4H), 4.03 (s, 2H), 4.17~4.40(m, 2H), 6.80~8.27(m, 6H) |
| 17 | O | —CH(CH₃)CH₂OCH₃ | mp (°C.) 78.9~79.3 | 50.96 | 3.83 | 3.13 | 50.88 | 3.90 | 3.08 | 1.23(d, 3H), 3.30(s, 3H), 3.97(s, 2H), 4.73~5.23(m, 1H), 6.73~8.20(m, 6H) |
| 18 | O | —CH₂SCH₃ | mp (°C.) 63.0~63.5 | 46.85 | 3.01 | 3.21 | 46.81 | 2.98 | 3.26 | 2.16(s, 3H), 3.97(s, 2H), 4.07(s, 2H), 6.67~8.13(m, 6H) |
| 19 | O | —CH₂CH₂SCH₃ | mp (°C.) 58.6~59.2 | 48.06 | 3.37 | 3.11 | 48.13 | 3.41 | 3.07 | 2.10(s, 3H), 2.50~2.93(m, 2H), 3.97 (s, 2H), 6.73~8.23(m, 6H) |
| 20 | O | —CH₂CH₂SC₂H₅ | mp (°C.) 42.8~42.3 | 49.19 | 3.70 | 3.02 | 49.16 | 3.61 | 2.96 | 1.23(t, 3H), 2.33~2.93(m, 4H), 3.97 (s, 2H), 4.23(t, 2H), 6.70~8.23(m, 6H) |
| 21 | O | —CH₂CH₂SCH₂CH=CH₂ | Viscous liquid* | 50.47 | 3.61 | 2.94 | 50.41 | 3.68 | 2.94 | 2.33(t, 2H), 3.07(d, 2H), 3.97(s, 2H), 4.23(t, 2H), 4.87~5.97(m, 3H), 6.80~8.23(m, 6H) |
| 22 | O | —CH₂CH₂SCH₂—C₆H₅ | mp (°C.) 40.4~41.2 | 54.80 | 3.65 | 2.66 | 54.87 | 3.71 | 2.61 | 2.60(t, 2H), 3.63(s, 2H), 3.93(s, 2H), 4.16(t, 2H), 6.77~8.20(m, 6H) |
| 23 | O | —CH₂CH₂Cl | mp (°C.) 84.1~84.9 | 46.59 | 2.76 | 3.19 | 46.65 | 2.68 | 3.24 | 3.67(t, 2H), 4.03(s, 2H), 4.26(d, 3H), 6.83~8.33(m, 6H) |
| 24 | O | —CH₂CH₂Br | mp (°C.) 76.3~77.2 | 42.30 | 2.50 | 2.90 | 42.50 | 2.39 | 2.75 | 3.46(t, 2H), 4.00(s, 2H), 4.36(t, 3H) 6.76~8.23(m, 6H) |
| 25 | O | —CH₂CH₂OH | mp (°C.) 49.0~50.5 | 48.64 | 3.12 | 3.33 | 48.77 | 3.05 | 3.27 | 2.33(b, 1H), 3.60~4.36(m, 7H) 6.70~8.23(m, 6H) |
| 26 | O | —CH₂CH₂OCCH₃ (O) | Viscous liquid* | 49.41 | 3.27 | 3.03 | 49.36 | 3.16 | 3.15 | 2.05(s, 3H), 4.00(s, 2H), 4.23(s, 4H) 6.60~8.16(m, 6H) |
| 27 | O | —CH₂CN | mp (°C.) 115.7~116.4 | 49.23 | 2.43 | 6.75 | 49.40 | 2.31 | 6.66 | 4.03(s, 2H), 4.63(s, 2H) 6.73~8.30(m, 6H) |
| 28 | O | —CH₂CH₂CN | mp (°C.) 87.4~88.4 | 50.42 | 2.82 | 6.53 | 50.29 | 2.96 | 6.60 | 2.67(t, 2H), 4.02(s, 2H), 4.27(t, 2H) 6.70~8.30(m, 6H) |
| 29 | O | —CH₂CH₂N(CH₃)₂ | mp (°C.) 72.5~72.7 | 51.07 | 4.06 | 6.26 | 51.19 | 4.12 | 6.18 | 2.27(s, 6H), 2.53(t, 2H), 4.00(s, 2H) 4.20(t, 2H), 6.73~8.26(m, 6H) |
| 30 | O | —CH₂CCH₃ (O) | mp (°C.) 103.4~103.7 | 50.07 | 3.03 | 3.24 | 50.00 | 3.10 | 3.36 | 2.10(s, 3H), 4.07(s, 2H), 4.53(s, 2H) 6.70~8.16(m, 6H) |
| 31 | S | —CH₂CH₂OH | Viscous liquid* | 46.85 | 3.00 | 3.21 | 46.98 | 2.89 | 3.09 | 2.13(s, 1H), 3.20(t, 2H), 4.23(s, 2H) 4.50(t, 2H), 6.76~8.23(m, 6H) |
| 32 | O | —CH₂CH=CHCl | Viscous liquid* | 48.02 | 2.68 | 3.11 | 48.20 | 2.57 | 3.04 | 4.00(s, 2H), 4.50~5.98(m, 2H) 5.70~6.50(m, 2H), 6.80~8.33(m, 6H) |
| 33 | O | —CH₂-(furan) | mp (°C.) 67.5~68.4 | 52.70 | 2.87 | 3.07 | 52.72 | 2.99 | 3.20 | 3.97(s, 2H), 4.40(s, 1H), 5.05(s, 2H) 6.20~6.45(m, 2H), 6.73~8.23(m, 6H) |
| 34 | O | —CH₂CH—CH₂ (O epoxide) | Viscous liquid* | 50.07 | 3.03 | 3.24 | 50.22 | 3.12 | 3.41 | 2.46~3.34(m, 3H), 3.77~4.56(m, 2H), 4.03(s, 2H), 6.80~8.23(m, 6H) |
| 35 | O | —CH₂CF₃ | mp (°C.) 64.0~65.2 | 44.61 | 2.20 | 3.06 | 44.83 | 2.26 | 3.19 | 4.07(s, 2H), 4.47(q, 2H) 6.80~8.34(m, 6H) |

TABLE 1-continued

Structure: 4-CF$_3$, 2-Cl-phenoxy linked to phenyl (with NO$_2$) bearing $-CH_2\overset{\underset{\displaystyle O}{\|}}{C}-X-R^8$

| Compound No. | X | R$^8$ | Physical Properties | Calculated C | Calculated H | Calculated N | Found C | Found H | Found N | $^1$H—NMR Spectral Data (δ:CDCl$_3$) |
|---|---|---|---|---|---|---|---|---|---|---|
| 36 | O | $-CH_2-\underset{\underset{\displaystyle Cl}{\|}}{C}=CH_2$ | mp (°C.) 48.5~49.5 | 44.83 | 2.50 | 2.90 | 44.98 | 2.63 | 2.78 | 4.06(s, 2H), 4.67(s, 2H), 5.33~5.52 (m, 2H), 6.68~8.33(m, 6H) |
| 37 | O | $-CH_2COOCH_3$ | mp (°C.) 79.2~80.1 | 48.08 | 2.15 | 3.73 | 48.20 | 2.01 | 3.92 | 3.70(s, 3H), 4.06(s, 2H), 4.60 (s, 2H), 6.77~8.23(m, 6H) |
| 38 | O | $-CH_2COOC_2H_5$ | Viscous liquid* | 49.41 | 3.27 | 3.03 | 49.61 | 3.35 | 3.18 | 1.27(t, 3H), 4.10(s, 2H), 4.16(q, 2H), 4.60(s, 2H), 6.73~8.23(m, 6H) |
| 39 | O | $-CH_2COOi-C_3H_7$ | Viscous liquid* | 50.48 | 3.60 | 2.94 | 50.54 | 3.49 | 2.81 | 1.25(d, 6H), 4.10(d, 2H), 4.56(s, 2H), 3.00(m, 1H), 6.77~8.23(m, 6H) |
| 40 | O | $-CH_2COOCH_2CH=CH_2$ | Viscous liquid* | 50.70 | 3.19 | 2.95 | 50.84 | 3.10 | 3.06 | 4.07(s, 2H), 4.57(s, 2H), 4.43~6.33 (m, 5H), 6.70~8.20(m, 6H) |
| 41 | O | $-CH_2COOCH_2C\equiv CH$ | Viscous liquid* | 50.91 | 2.77 | 2.96 | 50.87 | 2.73 | 2.87 | 2.50(m, 1H), 4.12(s, 2H), 4.56~4.77 (m, 4H), 6.70~8.03(m, 6H) |
| 42 | O | $-CH_2COOH$ | mp (°C.) 99.5~101.0 | 47.07 | 2.55 | 3.22 | 47.21 | 2.62 | 3.17 | 4.10(s, 2H), 4.67(s, 2H), 6.70~8.30 (m, 6H), 10.83(b, 1H) |
| 43 | O | $-CH_2CONH_2$ | mp (°C.) 101.0~102.5 | 47.18 | 2.79 | 6.47 | 47.29 | 2.70 | 6.55 | 4.03(s, 2H), 4.53(s, 2H), 6.60(b, 2H), 6.70~8.26(m, 6H) |
| 44 | O | $-CH_2CONHCH_3$ | Viscous liquid* | 48.39 | 3.15 | 6.27 | 48.32 | 3.08 | 6.15 | 3.70(s, 3H), 4.03(s, 2H), 4.56(s, 2H), 6.70~8.20(m, 6H) |
| 45 | O | $-CH_2CON(C_2H_5)_2$ | Viscous liquid* | 51.59 | 4.12 | 5.73 | 51.71 | 4.16 | 5.88 | 0.94~1.40(m, 6H), 2.97~3.60(m, 4H), 4.09(s, 2H), 4.73(s, 2H), 6.76~8.26(m, 6H) |
| 46 | O | $-CH_2CON(OCH_3)(CH_3)$ | Viscous liquid* | 47.86 | 3.38 | 5.87 | 47.80 | 3.29 | 5.96 | 3.13(s, 3H), 3.67(s, 3H), 4.10 (s, 2H), 4.82(s, 2H), 6.70~8.23 (m, 6H) |
| 47 | S | $-CH_2COOC_2H_5$ | $n_D^{26}$ 1.5578 | 47.75 | 3.16 | 2.93 | 47.90 | 3.11 | 3.03 | 1.27(t, 3H), 3.73(s, 2H), 3.90~4.43(m, 4H), 6.90~8.36(m, 6H) |
| 48 | O | $-CH(CH_3)COOCH_3$ | mp (°C.) 72.1~72.9 | 49.41 | 3.27 | 3.03 | 49.55 | 3.19 | 3.20 | 1.43(d, 3H), 3.70(s, 3H), 4.08 (s, 2H), 5.10(q, 1H), 6.70~8.26 (m, 6H) |
| 49 | O | $-CH(CH_3)COOC_2H_5$ | mp (°C.) 52.0~52.6 | 50.48 | 3.60 | 2.94 | 50.51 | 3.48 | 2.81 | 1.23(t, 3H), 1.47(d, 3H), 4.03 (s, 2H), 4.13(q, 2H), 5.03(q, 1H), 6.70~8.13(m, 6H) |
| 50 | O | $-CH(CH_3)COOn-C_3H_7$ | Viscous liquid* | 51.49 | 3.90 | 2.85 | 51.63 | 3.76 | 2.69 | 0.70~2.00(m, 8H), 4.00(s, 2H), 4.03(t, 2H), 5.06(q, 1H), 6.70~8.23(m, 6H) |
| 51 | O | $-CH(CH_3)COOi-C_3H_7$ | mp (°C.) 48.3~48.7 | 51.49 | 3.90 | 2.85 | 51.58 | 3.83 | 2.79 | 1.22(d, 6H), 1.45(d, 2H), 4.03 (s, 2H), 5.00(q, 2H), 6.73~8.23 (m, 6H) |
| 52 | O | $-CH(CH_3)COOCH_2CH=CH_2$ | Viscous liquid* | 51.70 | 3.51 | 2.87 | 51.88 | 3.39 | 2.65 | 1.50(d, 3H), 4.06(s, 2H DL racemic modification included), 4.60(d, 2H), 4.93-6.30(m, 3H), 6.76-8.26(m, 6H) |
| 53 | O | $-CH(CH_3)COOCH_2C\equiv CH$ | Viscous liquid* | 51.92 | 3.11 | 2.88 | 52.08 | 3.17 | 2.77 | 1.50(d, 3H), 1.47(m, 1H), 4.06 (s, 2H, racemic modification included), 4.77(d, 2H), 5.09(q, 1H), 6.76-8.30(m, 6H) |
| 54 | O | $-CH(CH_3)COOH$ | Viscous liquid* | 48.28 | 2.92 | 3.12 | 48.14 | 2.96 | 3.00 | 1.53(d, 3H), 4.06(s, 2H), 5.09 (b, 1H), 6.73~8.23(m, 6H) |
| 55 | O | $-CH(CH_3)COOCH_2CH_2OCH_3$ | mp (°C.) 38.0~41.0 | 49.85 | 3.76 | 2.77 | 50.01 | 3.66 | 2.90 | 1.55(d, 3H), 3.34(s, 3H), 3.40~4.40(m, 6H), 5.13(q, 1H), 6.83~8.33(m, 6H) |

TABLE 1-continued

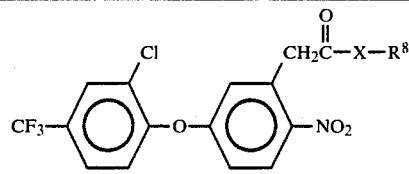

| Compound No. | X | R⁸ | Physical Properties | Elemental Analysis Calculated C | H | N | Found C | H | N | ¹H—NMR Spectral Data (δ:CDCl₃) |
|---|---|---|---|---|---|---|---|---|---|---|
| 56 | O | —CH₂CH₂COOC₂H₅ | mp (°C.) 95.6~96.7 | 50.48 | 3.60 | 2.94 | 50.61 | 3.48 | 2.88 | 1.22(t, 3H), 2.63(t, 2H), 3.98 (s, 2H), 4.10(q, 2H), 4.36(t, 2H), 6.70~8.25(m, 6H) |
| 57 | O | CH₃<br>\|<br>—CHCOOCH₂COOC₂H₅ | Viscous liquid* | 49.49 | 3.58 | 2.62 | 49.57 | 3.52 | 2.75 | 1.23(t, 3H), 1.57(d, 3H), 4.00~4.43(m, 4H), 4.60(d, 2H), 5.20(q, 1H), 6.70~8.33(m, 6H) |

*Viscous liquid at room temperature just after preparation
s: singlet, d: doublet, t: triplet, m: multiplet, b: broad

TABLE 2

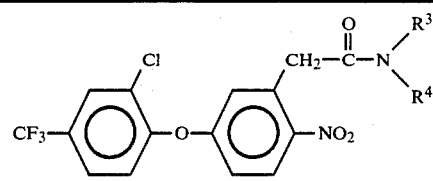

| Compound No. | R³ | R⁴ | Physical Properties | Elemental Analysis Calculated C | H | N | Found C | H | N | ¹H—NMR Spectral Data (δ: CDCl₃) |
|---|---|---|---|---|---|---|---|---|---|---|
| 58 | —H | —H | mp (°C.) 145.5~146.5 | 48.08 | 2.68 | 7.47 | 48.15 | 2.61 | 7.58 | 3.88(s, 2H), 5.87(b, 2H) 6.70~8.27(m, 6H) |
| 59 | —C₂H₅ | —H | mp (°C.) 188.7~189.3 | 50.69 | 3.50 | 6.95 | 50.62 | 3.56 | 7.03 | 1.10(t, 3H), 3.17(m, 2H), 3.87(s, 2H) 6.77~8.30(m, 7H) |
| 60 | —n-C₃H₇ | —H | mp (°C.) 175~176 | 58.87 | 3.86 | 6.72 | 58.99 | 3.70 | 6.81 | 1.00(t, 3H), 1.50(m, 2H), 3.23(t, 2H) 3.80(s, 2H), 5.80(b, 1H), 6.69~8.27 (m, 6H) |
| 61 | —i-C₃H₇ | —H | mp (°C.) 182.5~183.5 | 58.87 | 3.86 | 6.72 | 58.85 | 3.92 | 6.70 | 1.17(d, 6H), 3.83(s, 2H), 3.90(m, 1H) 5.65(b, 1H), 6.70~8.23(m, 1H) |
| 62 | —n-C₄H₉ | —H | mp (°C.) 149~150 | 52.97 | 4.21 | 6.50 | 53.00 | 4.15 | 6.58 | 0.90~2.05(m, 7H, 3.23(m, 2H), 3.80(s, 2H), 5.90(b, 1H), 6.69~8.23(m, 6H) |
| 63 | —i-C₄H₉ | —H | mp (°C.) 159.7~160.5 | 52.97 | 4.21 | 6.50 | 53.06 | 4.19 | 6.47 | 0.91(d,6H), 1.43~2.00 (m, 1H), 3.03(t, 2H), 3.73(s, 2H), 5.97(b, 1H), 6.70~8.17(m, 6H) |
| 64 | —t-C₄H₉ | —H | mp (°C.) 126~127 | 52.97 | 4.21 | 6.50 | 52.81 | 4.29 | 6.63 | 1.30(s, 9H), 3.73(s, 2H), 5.63(b, 1H) 6.67~8.13(m, 6H) |
| 65 | —n-C₂₅H₁₁ | —H | mp (°C.) 151.5~152.8 | 54.00 | 4.53 | 6.29 | 54.11 | 4.49 | 6.18 | 0.90~1.80(m, 9H), 3.17(m, 2H), 3.80(s, 2H), 5.63(b, 1H), 6.60~8.13(m, 6H) |
| 66 | —n-C₇H₁₅ | —H | mp (°C.) 133~134 | 55.87 | 5.11 | 5.92 | 55.93 | 5.22 | 5.81 | 0.90~2.00(m, 13H), 3.23(m, 2H), 3.77(s, 2H), 5.86(b, 1H), 6.70~8.20(m, 6H) |
| 67 | —CH₂—CH—CH₃<br>       \|<br>       OH | —H | mp (°C.) 145~146 | 49.95 | 3.72 | 6.47 | 49.99 | 3.81 | 6.42 | 1.20(d, 3H), 3.00~3.70(m, 3H), 3.87(s, 2H), 6.48(b, 1H), 6.73~8.16(m, 6H) |
| 68 | —CH₂—CH—C₂H₅<br>       \|<br>       OH | —H | mp (°C.) 144.8~145.6 | 51.07 | 4.06 | 6.26 | 51.20 | 3.98 | 6.14 | 0.93(t, 3H), 1.50(m, 2H), 3.00~3.80(m, 3H), 3.83(s, 2H), 6.40(b, 1H) 6.73~8.23(m, 6H) |
| 69 | —CH₂CH₂OCH₃ | —H | mp (°C.) 137.5~138.5 | 49.95 | 3.72 | 6.47 | 50.10 | 3.88 | 6.41 | 3.30~3.50(m, 7H), 3.83(s, 2H), 6.20(b, 1H), |

TABLE 2-continued

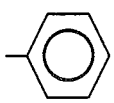

| Compound No. | R³ | R⁴ | Physical Properties | Elemental Analysis Calculated C | H | N | Found C | H | N | ¹H—NMR Spectral Data (δ: CDCl₃) |
|---|---|---|---|---|---|---|---|---|---|---|
| 70 | —CH₂CH=CH₂ | —H | mp (°C.) 174~175 | 52.12 | 3.40 | 6.75 | 52.18 | 3.29 | 6.71 | 6.67~8.20(m, 6H) 3.70~4.00(m, 4H), 4.90~5.30(m, 2H) 5.70(b, 1H), 6.73~8.16(m, 6H) |
| 71 | 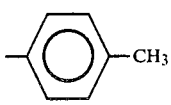 | —H | mp (°C.) 166.5~167.5 | 55.95 | 3.13 | 6.21 | 56.07 | 3.20 | 6.42 | 3.97(s, 2H), 6.67~8.16(m, 12H) |
| 72 | 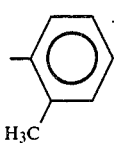 | —H | mp (°C.) 180.5~181.8 | 56.84 | 3.46 | 6.02 | 56.91 | 3.40 | 6.31 | 2.27(s, 3H), 3.90(s, 2H) 6.63~8.13(m, 11H) |
| 73 | 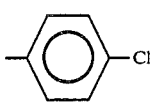 | —H | mp (°C.) 165~166 | 56.84 | 3.46 | 6.02 | 56.96 | 3.41 | 6.17 | 2.27(s, 3H), 3.90(s, 2H) 6.70~8.16(m, 11H) |
| 74 | 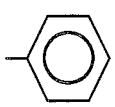 | —H | mp (°C.) 186.5~187.7 | 51.98 | 2.70 | 5.77 | 51.92 | 2.83 | 5.69 | 3.93(s, 2H), 6.73~8.20(m, 10H) 8.95(b, 1H) [DMSO—d₆ + CDCl₃] |
| 75 | —C₂H₅ | —C₂H₅ | mp (°C.) 117~118 | 52.97 | 4.21 | 6.50 | 52.88 | 4.31 | 6.54 | 0.93~1.47(m, 6H), 3.31(q, 4H), 3.97(s, 2H) 6.70~8.16(m, 6H) |
| 76 | 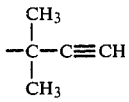 | —CH₃ | mp (°C.) 112.8~113.6 | 56.84 | 3.46 | 6.02 | 56.96 | 3.50 | 6.13 | 3.27(s, 3H), 3.70(s, 2H), 6.63~8.20(m, 11H) |
| 77 | —CH₂CN | —H | mp (°C.) 152.6~153.5 | 49.35 | 2.67 | 10.15 | 49.45 | 2.59 | 10.24 | 3.76~4.16(m, 4H), 6.76~8.23(m, 6H) 8.60(b, 1H) [DMSO—d₆ + CDCl₃] |
| 78 | —CH₂CH₂Cl | —H | mp (°C.) 145.4~146.3 | 46.70 | 2.99 | 6.40 | 46.90 | 3.10 | 6.51 | 3.46~3.67(m, 4H), 3.80(s, 2H) 6.23(b, 1H), 6.63~8.13(m, 6H) |
| 79 | —C(CH₃)₂—C≡CH | —H | mp (°C.) 140.3~140.8 | 54.49 | 3.65 | 6.35 | 54.58 | 3.55 | 6.42 | 1.63(s, 6H), 2.30(s, 1H), 3.80(s, 2H) 5.98(b, 1H), 6.67~8.23(m, 6H) |
| 80 | —n-C₃H₇ | —n-C₃H₇ | mp (°C.) 63.2~63.8 | 54.96 | 4.83 | 6.10 | 55.09 | 4.79 | 6.21 | 0.60~2.00(m, 10H), 3.03~3.50(m, 4H) 4.03(s, 2H), 6.70~8.20(m, 6H) |
| 81 | —CH₂CH=CH₂ | —CH₂CH=CH₂ | mp (°C.) 44.0~44.8 | 55.45 | 3.98 | 6.15 | 55.58 | 4.11 | 6.04 | 3.73~4.07(m, 6H), 4.86~5.98(m, 6H) 6.70~8.23(m, 6H) |
| 82 | —C₂H₅ | —i-C₃H₇ | mp (°C.) 75.6~75.7 | 54.00 | 4.53 | 6.29 | 54.13 | 4.39 | 6.18 | 1.93~1.50(m, 9H), 3.03~3.63(m, 2H), 4.03(s, 2H), 4.40~4.83(m, 1H), 6.77~8.26(m, 6H) |
| 83 | —CH₂CH₂OC₂H₅ | —H | mp (°C.) | 51.07 | 4.06 | 6.26 | 50.98 | 4.11 | 6.15 | 1.16(t, 3H), |

TABLE 2-continued

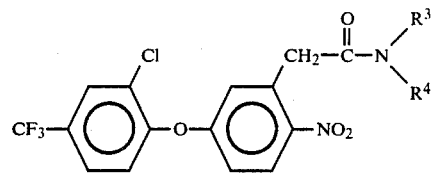

| Compound No. | R³ | R⁴ | Physical Properties | Elemental Analysis Calculated C | H | N | Found C | H | N | ¹H—NMR Spectral Data (δ: CDCl₃) |
|---|---|---|---|---|---|---|---|---|---|---|
| 84 | —CH₂CH₂CH₂OCH₃ | —H | mp (°C.) 124.6~125.5 132.3~132.6 | 51.07 | 4.06 | 6.26 | 51.21 | 3.92 | 6.33 | 3.30~3.73(m, 6H), 3.82(s, 2H) 6.16(b, 1H), 6.70~8.16(m, 6H) 1.50~1.96(m, 2H), 2.95~3.60(m, 7H), 3.82(s, 2H), 6.50(b, 1H), 6.70~8.23(m, 6H) |
| 85 | —CH₂CH(OCH₃)(OCH₃) | —H | mp (°C.) 116.6~117.1 | 49.30 | 3.92 | 6.05 | 49.48 | 3.77 | 6.21 | 1.20(t, 6H), 3.33~4.10(m, 8H), 4.63(t, 1H), 6.27(b, 1H), 6.86~8.37(m, 6H) |
| 86 | —CH₂CH₂S—sec-C₄H₉ | —H | mp (°C.) 105.5~105.7 | 51.37 | 4.51 | 5.70 | 51.50 | 4.60 | 5.59 | 0.76~1.73(m, 8H), 2.70(m, 3H), 3.47(q, 2H) 3.90(s, 2H), 6.31(b, 1H), 6.77~8.20(m, 6H) |
| 87 | —CH₂CH₂SCH₂CH=CH₂ | —H | mp (°C.) 105.2~105.3 | 50.58 | 3.82 | 5.89 | 50.47 | 3.91 | 5.88 | 2.53(t, 2H), 2.96~3.63(m, 4H), 3.80(s, 2H) 4.73~6.46(m, 4H), 6.67~8.17(m, 6H) |
| 88 | —CH₂CH₂SCH₂—C₆H₅ | —H | mp (°C.) 111.1~111.6 | 54.91 | 3.84 | 5.33 | 55.12 | 3.76 | 5.48 | 2.50(t, 3H), 3.32(q, 2H), 3.63(s, 2H), 3.73(s, 2H), 6.16(b, 1H), 6.70~8.10(m, 11H) |
| 89 | —CH₂CH₂O—n-C₄H₉ | —H | mp (°C.) 104.0~104.4 | 53.11 | 4.66 | 5.89 | 53.23 | 4.59 | 53.51 | 0.63~1.86(m, 7H), 3.16~3.68(m, 6H), 3.80(s, 2H), 6.13(b, 1H), 6.67~8.20(m, 6H) |
| 90 | —OCH₃ | —CH₃ | mp (°C.) 134~135 | 48.76 | 3.36 | 6.68 | 48.88 | 3.41 | 6.61 | 3.16(s, 3H), 3.76(s, 3H), 4.13(s, 2H) 6.70~8.22(m, 6H) |
| 91 | —OC₂H₅ | —C₂H₅ | mp (°C.) 90.1~90.4 | 51.07 | 4.06 | 6.26 | 51.21 | 4.22 | 6.41 | 1.20(t, 3H), 1.32(t, 3H), 3.65(q, 2H) 4.00(q, 2H), 4.13(s, 2H), 6.76~8.30(m, 6H) |
| 92 | —OCH₃ | —C₂H₅ | mp (°C.) 82.0~82.9 | 49.95 | 3.72 | 6.47 | 50.12 | 3.63 | 6.55 | 1.17(t, 3H), 3.67(q, 2H), 3.76(s, 3H) 4.13(s, 2H), 6.75~8.25(m, 6H) |
| 93 | —OCH₃ | —CH₂CH=CH₂ | mp (°C.) 98.7~99.6 | 51.77 | 2.74 | 6.35 | 51.80 | 2.68 | 6.44 | 3.67(s, 3H), 4.13(s, 2H), 4.20(d, 2H), 4.95~6.15(m, 3H), 6.70~8.20(m, 6H) | s: singlet, d: doublet, t: triplet, m: multiplet, b: broad

APPLICATION EXAMPLE

Preparation Example 1

(wettable powder)

25 Parts by weight of the compound of the present invention, 5 parts by weight of Sorpol 5039 (trade name of a product of Toho Chemical Industry Company) and 70 parts by weight of talc are thoroughly pulverized and mixed to obtain wettable powder.

Preparation Example 2

(emulsifiable concentrate)

5 Parts by weight of the compound of the present invention, 10 parts by weight of Sorpol 3005 X (a product of Toho Chemical Industry Company), 45 parts by weight of n-butanol and 40 parts by weight of xylene are thoroughly mixed to obtain emulsifiable concentrate.

Preparation Example 3

(granule)

1 Part by weight of the compound of the present invention, 45 parts by weight of bentonite, 44 parts by weight of clay, 5 parts by weight of sodium lignosulfonate and 5 parts by weight of sodium dodecylbenzenesulfonate are thoroughly pulverized and mixed. To the mixture is added water, and the resultant is thoroughly kneaded. The kneaded mixture is then subjected to granulation, followed by drying, thereby to obtain granule.

Preparation Example 4

(dust)

1 Part by weight of the compound of the present invention and 99 parts by weight of clay are thoroughly pulverized and mixed to obtain dust.

Application Example 1

(Postemergence application)

Pots each having a surface area of 1/5000 a were packed with paddy field soil in a greenhouse. In each pot were transplanted rice seedlings of 3.0 leaf stage at a depth of 2 to 3 cm from the surface soil. Seeds of barnyardgrass and monochoria, seeds of broad-leaved annual weeds, rotala spp and false pimpernel, and seeds of perennial weed, "Hotarui" (*Scirpus juncoides*), were mixed with dry paddy field soil and incorporated into the surface soil. When the barnyardgrass grew up to 0.5 to 1.0 leaf stage, an emulsifiable concentrate having a predetermined concentration (Preparation Example 2) was dropwise applied by means of a pipette. 21 Days after the application, phytotoxicity to rice plants and herbicidal effects on weeds were observed. The results obtained are shown in Table 3. The values indicated in Table 3 are based on the following criterion.

5: Perfect inhibition
4: 80% inhibition
3: 60% inhibition
2: 40% inhibition
1: 20% inhibition
0: No effect

TABLE 3

| Compound No. | Dosage (g/10a) | Herbicidal Effect | | | | Phytotoxicity to rice plant |
|---|---|---|---|---|---|---|
| | | Barnyard grass | Monochoria | Broad-leaved weeds | Hotarui (*Scirpus juncoides*) | |
| 2 | 30 | 5 | 5 | 5 | 5 | 0 |
| | 15 | 5 | 4 | 5 | 4 | 0 |
| 3 | 30 | 5 | 5 | 5 | 5 | 0 |
| | 15 | 4 | 3 | 5 | 2 | 0 |
| 5 | 30 | 5 | 5 | 5 | 5 | 1 |
| | 15 | 5 | 4 | 5 | 3 | 0 |
| 15 | 30 | 5 | 5 | 5 | 5 | 0 |
| | 15 | 5 | 5 | 5 | 5 | 0 |
| 16 | 30 | 5 | 5 | 5 | 5 | 1 |
| | 15 | 5 | 5 | 5 | 5 | 0 |
| 17 | 30 | 5 | 5 | 5 | 5 | 1 |
| | 15 | 5 | 5 | 5 | 5 | 0 |
| 21 | 30 | 5 | 4 | 5 | 4 | 0 |
| | 15 | 4 | 3 | 5 | 2 | 0 |
| 23 | 30 | 5 | 5 | 5 | 5 | 1 |
| | 15 | 5 | 4 | 5 | 4 | 0 |
| 26 | 30 | 5 | 5 | 5 | 5 | 0 |
| | 15 | 5 | 4 | 5 | 4 | 0 |
| 32 | 30 | 5 | 5 | 5 | 4 | 1 |
| | 15 | 5 | 4 | 5 | 3 | 0 |
| 37 | 30 | 5 | 5 | 5 | 5 | 1 |
| | 15 | 5 | 4 | 5 | 4 | 0 |
| 38 | 30 | 5 | 5 | 5 | 5 | 1 |
| | 15 | 5 | 4 | 5 | 4 | 0 |
| 40 | 30 | 5 | 5 | 5 | 5 | 0 |
| | 15 | 5 | 5 | 5 | 4 | 0 |
| 41 | 30 | 5 | 5 | 5 | 5 | 0 |
| | 15 | 5 | 4 | 5 | 4 | 0 |
| 44 | 30 | 5 | 5 | 5 | 5 | 1 |
| | 15 | 5 | 4 | 5 | 4 | 0 |
| 47 | 30 | 5 | 5 | 5 | 4 | 0 |
| | 15 | 5 | 4 | 5 | 3 | 0 |
| 48 | 30 | 5 | 5 | 5 | 5 | 0 |
| | 15 | 5 | 5 | 5 | 5 | 0 |
| 49 | 30 | 5 | 5 | 5 | 5 | 1 |
| 53 | 15 | 5 | 5 | 5 | 5 | 0 |
| | 30 | 5 | 5 | 5 | 5 | 1 |
| 58 | 15 | 5 | 5 | 5 | 4 | 0 |
| | 60 | 5 | 5 | 5 | 5 | 0 |
| 59 | 30 | 4 | 5 | 5 | 5 | 0 |
| | 60 | 5 | 5 | 5 | 5 | 0 |
| | 30 | 5 | 5 | 5 | 4 | 0 |
| 63 | 60 | 4 | 4 | 5 | 4 | 0 |
| | 30 | 2 | 2 | 5 | 2 | 0 |
| 66 | 60 | 4 | 4 | 5 | 5 | 0 |
| | 30 | 2 | 2 | 5 | 3 | 0 |
| 70 | 60 | 5 | 5 | 5 | 5 | 0 |
| | 30 | 4 | 5 | 5 | 4 | 0 |
| 75 | 60 | 5 | 5 | 5 | 4 | 0 |
| | 30 | 3 | 2 | 3 | 2 | 0 |
| 77 | 60 | 5 | 5 | 5 | 5 | 0 |
| | 30 | 5 | 5 | 5 | 4 | 0 |
| 83 | 60 | 5 | 5 | 5 | 5 | 0 |
| | 30 | 5 | 5 | 5 | 5 | 0 |
| 90 | 60 | 5 | 5 | 5 | 5 | 0 |
| | 30 | 5 | 5 | 5 | 4 | 0 |
| Comparative Compound No. 1 (Note 1) | 150 | 0 | 1 | 5 | 3 | 0 |
| | 75 | 0 | 1 | 5 | 2 | 0 |
| Comparative Compound No. 2 (Note 2) | 150 | 1 | 5 | 5 | 4 | 0 |
| | 75 | 0 | 1 | 5 | 3 | 0 |
| Comparative Compound No. 3 (Note 3) | 30 | 5 | 5 | 5 | 5 | 3 |
| | 15 | 5 | 4 | 5 | 4 | 2 |

Note 1.
Comparative Compound No. 1:

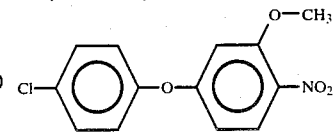

Note 2.
Comparative Compound No. 2:

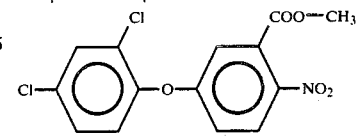

Note 3.
Comparative Compound No. 3:

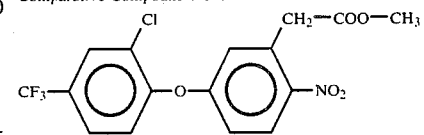

Application Example 2

(Preemergence application)

Pots each having a surface area of 1/5000 a were packed with paddy field soil in a greenhouse. Seeds of barnyardgrass and monochoria, seeds of broad-leaved annual weeds, rotala spp and false pimpernel, and seeds of perennial weeds, "Hotarui" (*Scirpus juncoides*), were mixed with dry paddy field soil and incorporated into the surface soil. Further, as the perennial weeds, tubers of arrowhead and flat sedge were transplanted. Thereafter, an emulsifiable concentrate having a predetermined concentration (Preparation Example 2) was dropwise applied by means of a pipette. 3 Days after the application, rice seedlings of 3.0 leaf stage were transplanted at a depth of 2 to 3 cm from the surface soil. 15 Days after the application, phytotoxicity to rice plants and herbicidal effects on weeds were observed. The results obtained are shown in Table 4. The criteria for the values indicated in Table 4 are the same as those employed in Application Example 1.

hours after the planting of the seeds. On the other hand, the postemergence application was effected by applying a composition in a dosage of 30 a.i. g/10a, when the soybean, the Indian corn and the weeds grew up to respectively 2 to 3 leaf stage, 3 to 4 leaf stage and 2 to 2.5 leaf stage. The herbicidal composition of the present invention was applied as follows. An emulsifiable concentrate having a predetermined concentration (Preparation Example 2) was diluted with 15 liters of water

TABLE 4

| | Dosage (g/10$^a$) | Barnyard grass | Monochoria | Broadleaved weeds | Hotarui (*Scirpus juncoides*) | Arrowhead | Flat sedge | Phytotoxicity to rice plant |
|---|---|---|---|---|---|---|---|---|
| Compound No. | | | | | | | | |
| 58 | 60 | 5 | 5 | 5 | 5 | 3 | 5 | 1 |
|  | 30 | 5 | 4 | 5 | 5 | 2 | 4 | 0 |
|  | 15 | 4 | 4 | 4 | 4 | 1 | 3 | 0 |
| 59 | 60 | 5 | 5 | 5 | 5 | 4 | 5 | 0 |
|  | 30 | 5 | 5 | 5 | 5 | 2 | 5 | 0 |
|  | 15 | 4 | 5 | 5 | 4 | 1 | 4 | 0 |
| 69 | 60 | 5 | 5 | 5 | 5 | 5 | 5 | 0 |
|  | 30 | 5 | 5 | 5 | 5 | 4 | 4 | 0 |
|  | 15 | 4 | 5 | 5 | 4 | 3 | 3 | 0 |
| Comparative | 150 | 2 | 3 | 5 | 4 | 2 | 1 | 0 |
| Compound No. 1 | 60 | 1 | 2 | 4 | 2 | 1 | 1 | 0 |
|  | 30 | 0 | 1 | 3 | 1 | 0 | 0 | 0 |
| Comparative | 60 | 4 | 5 | 5 | 3 | 1 | 3 | 5 |
| Compound No. 4 | 30 | 2 | 2 | 4 | 2 | 0 | 2 | 3 |
|  | 15 | 1 | 1 | 3 | 1 | 0 | 1 | 2 |

Comparative Compound No. 4:

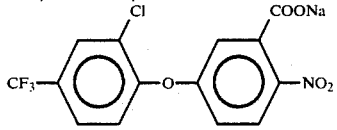

Application Example 3

Pots each having a surface area of 1/2500 a were packed with upland soil in a greenhouse. In each pot were planted seeds of soybean, Indian corn, large crabgrass, livid amaranth and "Oinutade" (*Polygonum nodosum*).

The preemergence application was effected, by applying a composition in a dosage of 30 a.i. g/10a, 24 hours per each are of the upland soil, and then applied by means of a glass sprayer. 14 Days after the application, the degree of the herbicidal effect on weeds was observed. 30 Days after the application, the degree of the phytotoxicity to crop plants was observed. The results obtained are shown in Table 5 The criteria for the values indicated in Table 5 are the same as those employed in Application Example 1.

TABLE 5

| | Herbicidal Activity and Phytotoxicity | | | | | | | | | |
|---|---|---|---|---|---|---|---|---|---|---|
| | Preemergence application | | | | | Postemergence application | | | | |
| Compound No. | Large crabgrass | Livid amaranth | Oinutade (*Polygonum nodosum*) | Soybean | Indian corn | Large crabgrass | Livid amaranth | Oinutade (*Polygonum nodosum*) | Soybean | Indian corn |
| 1 | 2 | 5 | 4 | 0 | 0 | 2 | 5 | 4 | 0 | 0 |
| 5 | 2 | 5 | 4 | 0 | 0 | 2 | 5 | 3 | 0 | 0 |
| 8 | 1 | 5 | 5 | 0 | 0 | 3 | 5 | 4 | 1 | 1 |
| 15 | 3 | 5 | 5 | 0 | 0 | 3 | 5 | 5 | 0 | 0 |
| 16 | 4 | 5 | 5 | 0 | 0 | 3 | 5 | 5 | 1 | 1 |
| 17 | 4 | 5 | 5 | 0 | 0 | 3 | 5 | 5 | 1 | 0 |
| 20 | 2 | 5 | 5 | 0 | 0 | 2 | 5 | 4 | 0 | 0 |
| 23 | 3 | 5 | 5 | 0 | 0 | 3 | 5 | 5 | 1 | 0 |
| 26 | 3 | 5 | 5 | 0 | 0 | 2 | 5 | 5 | 1 | 0 |
| 27 | 4 | 5 | 5 | 0 | 0 | 3 | 5 | 5 | 1 | 0 |
| 30 | 3 | 5 | 5 | 0 | 0 | 3 | 5 | 4 | 1 | 0 |
| 32 | 3 | 5 | 5 | 0 | 0 | 3 | 5 | 5 | 1 | 0 |
| 38 | 3 | 4 | 4 | 0 | 0 | 3 | 5 | 5 | 1 | 0 |
| 45 | 3 | 4 | 4 | 0 | 0 | 3 | 5 | 5 | 1 | 0 |
| 47 | 3 | 4 | 3 | 0 | 0 | 3 | 5 | 4 | 0 | 0 |
| 48 | 4 | 5 | 4 | 0 | 0 | 4 | 5 | 5 | 0 | 0 |
| 49 | 4 | 5 | 5 | 0 | 0 | 4 | 5 | 5 | 0 | 0 |
| 51 | 3 | 4 | 3 | 0 | 0 | 3 | 5 | 5 | 0 | 0 |
| 52 | 4 | 5 | 4 | 0 | 0 | 4 | 5 | 5 | 1 | 0 |
| 68 | 3 | 5 | 5 | 0 | 0 | 3 | 5 | 5 | 1 | 0 |
| 77 | 3 | 5 | 5 | 0 | 0 | 4 | 5 | 5 | 0 | 0 |
| 78 | 3 | 5 | 5 | 0 | 0 | 3 | 5 | 5 | 1 | 0 |
| 83 | 4 | 5 | 5 | 0 | 0 | 4 | 5 | 5 | 1 | 0 |

TABLE 5-continued

| | Herbicidal Activity and Phytotoxicity | | | | | | | | | |
|---|---|---|---|---|---|---|---|---|---|---|
| | Preemergence application | | | | | Postemergence application | | | | |
| Compound No. | Large crabgrass | Livid amaranth | Oinutade (*Polygonum nodosum*) | Soybean | Indian corn | Large crabgrass | Livid amaranth | Oinutade (*Polygonum nodosum*) | Soybean | Indian corn |
| 90 | 3 | 5 | 5 | 0 | 0 | 3 | 5 | 5 | 0 | 0 |
| Comparative compound No. 4 | 4 | 5 | 4 | 0 | 0 | 2 | 3 | 2 | 0 | 0 |

What is claimed is:

1. A compound represented by the formula

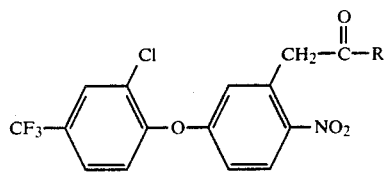

wherein R represents —OR¹ in which R¹ represents a straight or branched alkyl group substituted with at least one member selected from the group consisting of a hydroxyl group and a hydrocarbyloxy group, or a straight or branched alkyl group substituted with at least one member selected from the group consisting of a carboxyl group and a group functionally derived therefrom.

2. A compound according to claim 1, wherein R¹ represents a straight or branched alkyl group substituted with a hydrocarbyloxy group.

3. A compound according to claim 1, wherein R¹ represents a straight or branched alkyl group substituted with at least one member selected from the group consisting of a carboxyl group and a group functionally derived therefrom.

4. A compound according to claim 1, wherein R¹ represents a straight or branched alkyl group substituted with a halogen atom.

5. A compound according to claim 1 selected from the group consisting of:
1-methyl-2-methoxyethyl 2-nitro-5-(2'-chloro-4'-trifluoromethylphenoxy)phenylacetate,
2-methoxyethyl 2-nitro-5-(2'-chloro-4'-trifluoromethylphenoxy)phenylacetate,
2-hydroxyehtyl 2-nitro-5-(2'-chloro-4'-trifluoromethylphenoxy)phenylacetate,
1-methoxycarbonylethyl 2-nitro-5-(2'-chloro-4'-trifluoromethylphenoxy)phenylacetate, and
1-ethoxycarbonylethyl 2-nitro-5-(2'-chloro-4'-trifluoromethylphenoxy)phenylacetate.

6. A compound according to claim 1, wherein R is —OCH₂CH₂OCH₃.

7. A compound according to claim 1, wherein R is —OCH₂CH₂OC₂H₅.

8. A compound according to claim 1, wherein R is

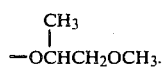

9. A compound according to claim 1, wherein R is

10. A compound according to claim 1, wherein R is

11. A herbicidal composition which comprises, together with an agriculturally acceptable carrier, as an active ingredient a herbicidally effective amount of a compound represented by the formula

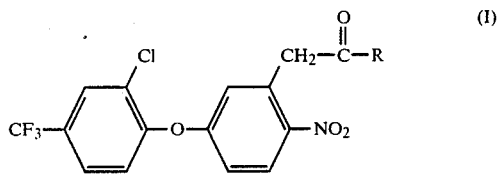

wherein R represents —OR¹ in which R¹ represents a straight or branched alkyl group substituted with at least one member selected from the group consisting of a hydroxyl group and a hydrocarbyloxy group or a straight or branched alkyl group substituted with at least one member selected from the group consisting of a carboxyl group and a group functionally derived therefrom.

12. A herbicidal composition according to claim 11, wherein R¹ represents a straight or branched alkyl group substituted with a hydrocarbyloxy group.

13. A herbicidal composition according to claim 11, wherein R¹ represents a straight or branched alkyl group substituted with at least one member selected from the group consisting of a carboxyl group and a group functionally derived therefrom.

14. A herbicidal composition according to claim 11, wherein R¹ represents a straight or branched alkyl group substituted with a hydroxyl group.

15. A herbicidal composition according to claim 11, wherein the active ingredient is at least one member selected from the group consisting of:
1-methyl-2-methoxyethyl 2-nitro-5-(2'-chloro-4'-trifluoromethylphenoxy)phenylacetate,
2-methoxyethyl 2-nitro-5-(2'-chloro-4'-trifluoromethylphenoxy) phenylacetate,
2-hydroxyethyl 2-nitro-5-(2'-chloro-4'-trifluoroemthylphenoxy)phenylacetate,
1-methoxycarbonylethyl 2-nitro-5-(2'-chloro-4'-trifluoromethylphenoxy)phenylacetate, and
1-ethoxycarbonylethyl 2-nitro-5-(2'-chloro-4'-trifluoromethylphenoxy)pheylacetate.

16. A method for the destruction of undesirable weeds, which comprises applying to said weeds a herbicidally effective amount of a compound represented by the formula

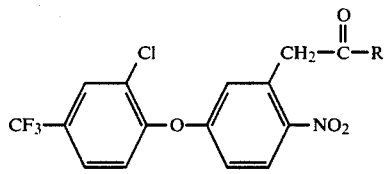

(I)

wherein R represents —OR$^1$ in which R$^1$ represents a straight or branched alkyl group substituted with at least one member selected from the group consisting of a hydroxyl group and a hydrocarbyloxy group, or a straight or branched alkyl group substituted with at least one member selected from the group consisting of a carboxyl group and a group functionally derived therefrom as such or in the form of a herbicidal composition comprising said compound of formula (I) as an active ingredient and an agriculturally acceptable carrier.

17. A method according to claim 16, wherein said compound is applied to a field where rice plants are growing.

* * * * *